United States Patent
Maximilien et al.

(10) Patent No.: US 12,138,351 B2
(45) Date of Patent: Nov. 12, 2024

(54) PHARMACEUTICAL COMPOSITION FOR ORAL ADMINISTRATION COMPRISING AMINOPYRIMIDINE DERIVATIVE OR PHARMACEUTICALLY ACCEPTABLE SALT, HYDRATE, OR SOLVATE THEREOF

(71) Applicant: Janssen Biotech, Inc., Horsham, PA (US)

(72) Inventors: Jacqueline Maximilien, Antwerp (BE); Gopal Rajan, Antwerp (BE)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/228,753

(22) Filed: Apr. 13, 2021

(65) Prior Publication Data

US 2021/0322323 A1    Oct. 21, 2021

Related U.S. Application Data

(60) Provisional application No. 63/014,277, filed on Apr. 23, 2020, provisional application No. 63/009,623, filed on Apr. 14, 2020.

(51) Int. Cl.

| | | |
|---|---|---|
| *A61K 9/28* | (2006.01) | |
| *A61K 9/00* | (2006.01) | |
| *A61K 9/20* | (2006.01) | |
| *A61K 31/5377* | (2006.01) | |

(52) U.S. Cl.
CPC ............ *A61K 9/284* (2013.01); *A61K 9/0053* (2013.01); *A61K 9/2009* (2013.01); *A61K 9/2018* (2013.01); *A61K 9/2054* (2013.01); *A61K 31/5377* (2013.01); *C07B 2200/13* (2013.01)

(58) Field of Classification Search
CPC ............ A61K 9/2054; A61K 31/5377; A61K 9/0053; A61K 9/2009; A61K 9/2018; A61K 9/284; A61P 35/00; C07B 2200/13
See application file for complete search history.

(56) References Cited

U.S. PATENT DOCUMENTS

| | | | |
|---|---|---|---|
| 6,437,006 B1 * | 8/2002 | Yoon ................... | A61K 9/4858 424/464 |
| 9,593,098 B2 | 3/2017 | Suh et al. | |
| 9,593,164 B2 | 3/2017 | Chiu et al. | |
| 2008/0131505 A1 * | 6/2008 | Li ....................... | A61K 9/1623 264/109 |
| 2011/0281912 A1 * | 11/2011 | Winter ................ | A61K 9/0056 514/319 |
| 2015/0224199 A1 * | 8/2015 | De Weer .............. | A61P 43/00 514/228.5 |
| 2016/0151380 A1 * | 6/2016 | Luckhart ............ | A61K 49/0008 514/227.8 |
| 2020/0360394 A1 | 11/2020 | Kang et al. | |

FOREIGN PATENT DOCUMENTS

| | | | | |
|---|---|---|---|---|
| WO | WO 2016/060443 A2 | 4/2016 | | |
| WO | WO 2017/176965 A1 | 10/2017 | | |
| WO | WO-2018136796 A1 * | 7/2018 | ............. | A61K 31/47 |
| WO | WO-2018194356 A1 * | 10/2018 | ......... | A61K 31/5377 |
| WO | WO 2019/022485 A1 | 1/2019 | | |
| WO | WO 2019/022486 A1 | 1/2019 | | |
| WO | WO 2019/022487 A1 | 1/2019 | | |
| WO | WO 2020/079637 A1 | 4/2020 | | |

OTHER PUBLICATIONS

International Search Report issued in corresponding PCT Patent Application No. PCT/IB2021/053035, filed on Apr. 13, 2021. Mailing Date of International Search Report: Jul. 1, 2021.

Written Opinion issued in corresponding PCT Patent Application No. PCT/IB2021/053035, filed on Apr. 13, 2021. Mailing Date of Written Opinion: Jul. 1, 2021.

\* cited by examiner

*Primary Examiner* — Andrew S Rosenthal
(74) *Attorney, Agent, or Firm* — BakerHostetler

(57) ABSTRACT

Provided herein are pharmaceutical compositions for oral administration comprising N-(5-(4-(4-((dimethylamino)methyl)-3-phenyl-1H-pyrazol-1-yl)pirimidine-2-ylamino)-4-methoxy-2-morpholinophenyl)acrylamide or a pharmaceutically acceptable salt, hydrate, or solvate thereof as an active ingredient; and a combination of (i) a cellulose derivative and (ii) a sugar or polyol as diluents. The disclosed compositions are characterized by improved manufacturability, while maintaining the pharmaceutical benefits of minimizing the effect according to changes in pH environment in the stomach, possessing excellent stability, and exhibiting good bioavailability.

28 Claims, 5 Drawing Sheets

PHARMACEUTICAL COMPOSITION FOR ORAL ADMINISTRATION COMPRISING AMINOPYRIMIDINE DERIVATIVE OR PHARMACEUTICALLY ACCEPTABLE SALT, HYDRATE, OR SOLVATE THEREOF

CROSS-REFERENCE TO RELATED APPLICATIONS

The present application claims the benefit of priority of U.S. Provisional Application No. 63/009,623, filed Apr. 14, 2020, and U.S. Provisional Application No. 63/014,277, filed Apr. 23, 2020, the entire contents of which are incorporated by reference herein.

TECHNICAL FIELD

The present disclosure relates to pharmaceutical compositions for oral administration comprising an aminopyrimidine derivative or pharmaceutically acceptable salt, hydrate, or solvate thereof. More particularly, the present disclosure relates to a pharmaceutical composition comprising N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) a pharmaceutically acceptable salt, hydrate, or solvate thereof.

BACKGROUND

WO 2016/060443 discloses an aminopyrimidine derivative, for example, N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or pharmaceutically acceptable salt, hydrate, or solvate thereof. Lazertinib or pharmaceutically acceptable salt, hydrate, or solvate thereof has activity of selectively inhibiting protein kinase, particularly, protein kinase for a mutant epidermal growth factor receptor, and may provide, for example, an effective and safe treatment method for non-small cell lung cancer. Lazertinib or pharmaceutically acceptable salt, hydrate, or solvate thereof has been known as irreversible EGFR TKI which has less effect on wild-type EGFR, strong inhibitory activity on T790M single active mutation (EGFRm) and double mutation, and excellent selectivity, and is expected to exhibit a therapeutically effective effect in the treatment of patients with primary cancer of progressive non-small cell lung cancer and progressive non-small cell lung cancer accompanied by brain metastasis.

When Lazertinib or pharmaceutically acceptable salt, hydrate, or solvate thereof is formulated as a composition for oral administration, it may be considered to formulate Lazertinib or pharmaceutically acceptable salt, hydrate, or solvate thereof in the form of an immediate-release pharmaceutical composition having a mechanism in which the active ingredient is immediately released in the stomach and then transferred to the small intestine to be absorbed. In the formulation of such an immediate-release pharmaceutical composition, it is required to minimize the effect of pH changes in the stomach, for example, according to foods or simultaneous-administered drugs (e.g., an antacid, etc.). For example, since pH in the empty stomach is not constant ranging from pH 1 to pH 3.5 and also an average pH in a postprandial stomach is pH 4 (pH 3 to 5), deviations in dissolution rate may occur depending on the physicochemical properties of an active ingredient, which may result in changes in absorption rate and bioavailability.

SUMMARY

The present inventors found that when N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or pharmaceutically acceptable salt, hydrate, or solvate thereof is formulated using a combination of specific diluents in specific relative proportions, it is possible to prepare an immediate-release pharmaceutical composition that has improved manufacturability, while maintaining the pharmaceutical benefits of minimizing the effect according to changes in pH environment in the stomach, possessing excellent stability, and exhibiting good bioavailability.

According to an aspect of the present disclosure, provided are pharmaceutical compositions for oral administration comprising N-(5-(4-(4-((dimethylamino)methyl)-3-phenyl-1H-pyrazol-1-yl)pirimidine-2-ylamino)-4-methoxy-2-morpholinophenyl)acrylamide or a pharmaceutically acceptable salt, hydrate, or solvate thereof as an active ingredient; and a combination of (i) a cellulose derivative and (ii) a sugar or polyol as diluents, wherein the cellulose derivative and the sugar or polyol are present in the pharmaceutical composition in a weight ratio of 1:0.10 to 1:0.40.

Also disclosed are methods for treating non-small cell lung cancer in a subject in need thereof, comprising administering to the subject a pharmaceutical composition of the above-described type.

DETAILED DESCRIPTION

Figure 1:
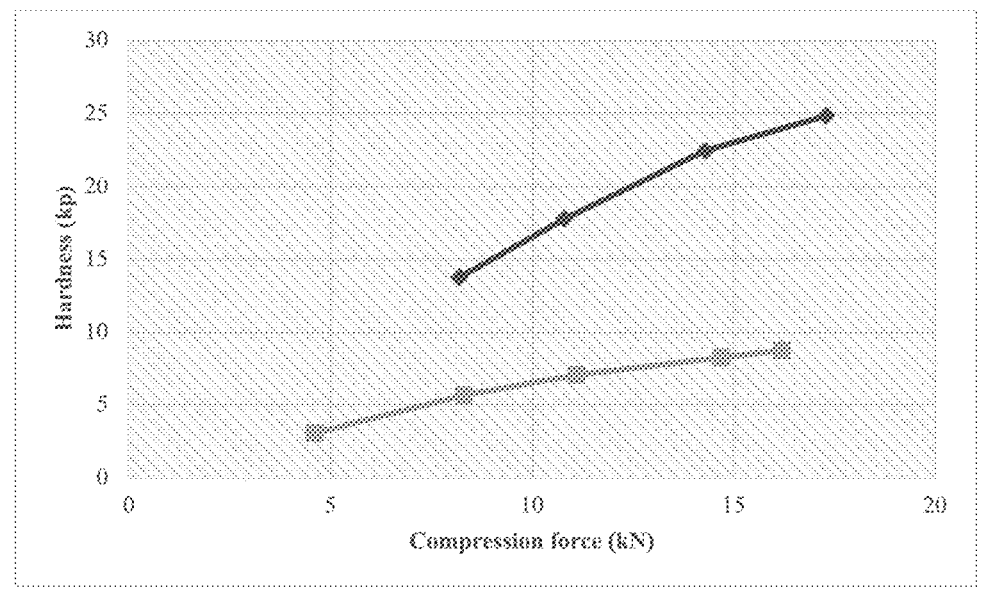
FIG. 1 illustrates the results of a compression force profile study that compares a composition according to the present disclosure with a prior formulation.

The present disclosure provides a pharmaceutical composition for oral administration comprising N-(5-(4-(4-((dimethylamino)methyl)-3-phenyl-1H-pyrazol-1-yl)pirimidine-2-ylamino)-4-methoxy-2-morpholinophenyl) acrylamide (Lazertinib) or a pharmaceutically acceptable salt, hydrate, or solvate thereof as an active ingredient; and a combination of (i) a cellulose derivative and (ii) a sugar or polyol as diluents, wherein the cellulose derivative and the sugar or polyol are present in the pharmaceutical composition in a weight ratio of 1:0.10 to 1:0.40.

In this specification, the 'diluent' and the 'additive' have the same meaning and may be used interchangeably. According to the present disclosure, it was found that when Lazertinib or pharmaceutically acceptable salt, hydrate, or solvate thereof is formulated using a combination of specific diluents in specific proportions, that is, a combination of a cellulose derivative and a sugar or polyol, it is possible to prepare an immediate-release pharmaceutical composition with excellent manufacturability that is capable of minimizing the effect according to changes in pH environment in the stomach. The changes in pH environment in the stomach include a pH change by diet; and a pH change by drugs, for example, a proton pump inhibitor such as esomeprazole or a H2-receptor antagonist such as cimetidine, an antacid, and the like, but is not limited thereto.

Lazertinib and methods of making Lazertinib are described, for example, in U.S. Pat. No. 9,593,098, which is incorporated by reference herein.

In the pharmaceutical composition of the present disclosure, N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or pharmaceutically acceptable salt, hydrate, or solvate thereof may be used in therapeutically effective amounts. For example, Lazertinib or a pharmaceutically acceptable salt, hydrate, or solvate thereof may be used in a range of 10 to 320 mg as Lazertinib per unit formulation (e.g., per unit tablet), and may be used in amounts of, for example, 10 mg, 20 mg, 40 mg, 80 mg, 100 mg, 120 mg, 160 mg, 240 mg, or 320 mg.

The pharmaceutical composition of the present disclosure includes a combination of specific diluents, including a combination of a cellulose derivative and a sugar or polyol. It has presently been discovered that when the weight ratio of a cellulose derivative to a sugar or polyol in the present compositions is 1:0.1 to 1:0.40, the resulting composition possesses superior manufacturability relative to previous formulations. In particular, when the respective components of the present compositions are combined, mixed, and subjected to compression in order to form a compressed tablet dosage form, a wide hardness profile is obtained within a given range of compression forces. As a result, the present compositions are compatible with, i.e., provide an acceptable hardness profile within, a wider range of compression forces than prior art formulations. This characteristic is described more fully in the examples, infra. At the same time, in the present compositions, Lazertinib or pharmaceutically acceptable salt, hydrate, or solvate thereof may minimize the effect according to changes in pH environment in the stomach.

In accordance with the present compositions, the weight ratio of cellulose derivative to sugar or polyol in the present compositions may be in a range of 1:0.1 to 1:0.40, such as from 1:0.15 to 1:0.40, from 1:0.20 to 1:0.30, or from 1:0.20 to 1:0.25.

Exemplary cellulose derivatives include cellulose esters and cellulose ethers. Cellulose esters include cellulose acetate (CA), cellulose acetate phthalate (CAP), Cellulose acetate butyrate (CAB), Cellulose acetate trimelitate (CAT), and hydroxupropylmethyl cellulose phthalate (HPMCP). Cellulose ethers include methyl cellulose, ethyl cellulose, hydroxylpropylcellulose (HPC), hydroxyethylcellulose (HEC), hydroxypropylmethylcellulose (HPMC), sodium carboxymethyl cellulose (NaCMC), and carboxymethylcellulose (CMC). The term "cellulose derivative" is intended to include alternative forms of cellulose, such as microcrystalline cellulose (MCC). Microcrystalline cellulose is available in a number of different forms, referred to as grades. Mechanical properties of MCC grades are greatly influenced by their particle size and degree of crystallization. In recent years, new grades of MCC have been prepared with improved pharmaceutical characteristics such as silicified MCC (SMCC) and second generation MCC grades or MCC type II (MCC-II). These grades are prepared by co-processing of cellulose with other substances such as colloidal silicon dioxide or by special chemical procedures. Other types of available pure cellulose are powdered cellulose (PC) and low crystallinity powdered cellulose (LCPC), which are also subsumed within the intended meaning of the term "cellulose derivative".

Sugars that may be used in the present composition include any of the mono- or disaccharides, including, for example, galactose, glucose, mannose, fructose, xylose, fucose, arabinose, sucrose, maltose, and lactose. Polyols include low molecular weight compounds, such as sugar alcohols. Maltitol, sorbitol, mannitol, xylitol, erythritol, ethylene glycol, glycerol, threitol, arabitol, ribitol, galactitol, fucitol, iditol, inositol, lactitol, and isomalt represent exemplary sugar alcohols. Other types of polyols include polymeric polyols, such as polyethylene oxide or polyethylene glycol (PEG) and polypropylene glycol (PPG).

Any combination of a cellulose derivative and sugar or polyol may be used in the present compositions. In some embodiments, the cellulose derivative is microcrystalline cellulose. In some embodiments, the sugar/polyol is mannitol. In accordance with the present compositions, the weight ratio of microcrystalline cellulose to mannitol in the present compositions may be in a range of 1:0.1 to 1:0.40, such as from 1:0.15 to 1:0.40, from 1:0.20 to 1:0.30, or from 1:0.20 to 1:0.25.

The total amount of the diluents (the cellulose derivative and sugar or polyol) in the present compositions may be about 55-80 wt %, based on the total weight of the composition. For example, the total amount of the diluents may be about 57-78 wt %, 58-77 wt %, 60-77 wt %, 62-77 wt %, or about 55, 56, 57, 58. 59, 60, 61, 62, 63, 64, 65, 66, 67 68, 69, 70, 71, 72, 73, 74, 75, 76, 77, 78, 79, or 80 wt %, based on the total weight of the composition.

In addition to the diluents, the pharmaceutical compositions according the present disclosure may include further excipients, such as a disintegrating agent, a lubricant, a glidant, colorants, or other common excipients.

When present, the disintegrating agent may be a conventional disintegrating agent used in the field of pharmaceutics. However, according to the present disclosure, in the case of using a specific disintegrating agent, that is, croscarmellose sodium among various disintegrating agents, the precipitation is significantly delayed when the drug disintegrated/dissolved in the stomach is transferred to the intestine. Accordingly, it is preferred that the pharmaceutical composition of the present disclosure includes croscarmellose sodium as a disintegrating agent. The croscarmellose sodium may be present, for example, in an amount of about 0.5 to 10 wt %, such as 1-10 wt %, 1-5 wt %, 2-5 wt %, 2-3 wt %, or 2.5-3 wt %, with respect to the total weight of the composition.

When present, the lubricant may be a conventional lubricant used in the field of pharmaceutics. However, according to the present disclosure, a specific lubricant, that is, magnesium stearate among various lubricants has particularly excellent compatibility with Lazertinib or pharmaceutically acceptable salt, hydrate, or solvate thereof, thereby securing excellent stability. Accordingly, it is preferred that the pharmaceutical composition of the present disclosure includes magnesium stearate as a lubricant. The magnesium stearate may be used in a sufficient amount to achieve a sufficient lubricating effect, and for example, may be present in an amount of about 0.4 to 2 wt %, such as 0.5-2 wt %, 0.75-1.25 wt %, or 1-2 wt % with respect to the total weight of the composition, but is not limited thereto. In a certain embodiment, the lubricant, such as magnesium stearate, is present in an amount of about 1 wt %.

The present dosage forms may further include a glidant. The glidant may be selected from among conventional examples used in the field of pharmaceutics. According to some embodiments, the glidant is colloidal silicon dioxide. In some embodiments, the colloidal silicon dioxide is hydrophobic silicon dioxide. The glidant, such as hydrophobic colloidal silicon dioxide, may be present in an amount of about 0.25-0.75 wt %, based on the total weight of the composition. For example, the glidant may be present in an amount of 0.25, 0.30, 0.40, 0.50, 0.60, 0.70, or 0.75 wt %. In a particular embodiment, the glidant is hydrophobic colloidal silicon dioxide that is present in an amount of 0.5 wt %.

In certain embodiments, the pharmaceutical composition of the present disclosure includes N-(5-(4-(4-((dimethylamino)methyl)-3-phenyl-1H-pyrazol-1-yl)pirimidine-2-ylamino)-4-methoxy-2-morpholinophenyl)acrylamide or a pharmaceutically acceptable salt, hydrate, or solvate thereof as an active ingredient; a combination of microcrystalline cellulose and mannitol as diluents; croscarmellose sodium as a disintegrating agent; and magnesium stearate as a lubricant. In certain embodiments, this composition further includes hydrophobic colloidal silicon dioxide.

In the present compositions, Lazertinib mesylate is excellent in stability, solubility, and bioavailability compared to the compound in the form of free-base and may be prepared with high purity. Further, there is an advantage that Lazertinib mesylate has excellent bioavailability even in the case of co-administration with, e.g., an antacid, as well as in the case of administration thereof alone. Accordingly, in the pharmaceutical compositions of the present disclosure, the active ingredient may be Lazertinib mesylate. In certain embodiments, the composition comprises 15-40 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 55-80 wt % of the combination of microcrystalline cellulose and mannitol; 2-3 wt % of croscarmellose sodium; and 0.5 to 2 wt % of magnesium stearate. In some embodiments, the pharmaceutical composition comprises 17-38 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 60 to 77 wt % of the combination of microcrystalline cellulose and mannitol; 2.5-3 wt % of croscarmellose sodium; and 0.75-1.25 wt % of magnesium stearate. Either of these embodiments may further comprise colloidal silicon dioxide, such as hydrophobic colloidal silicon dioxide, such as in an amount of about 0.50 wt %, based on the total weight of the composition.

Lazertinib mesylate may be a crystalline form. In one embodiment, Lazertinib mesylate may be a crystalline form having a PXRD pattern with peaks at 5.614, 12.394, 14.086, 17.143, 18.020, 19.104, 21.585, 22.131, and 22.487° 2θ±0.2° 2θ. In another embodiment, Lazertinib mesylate may be a crystalline form having a differential scanning calorimeter (DSC) thermogram with an endothermic peak at 210 to 230° C., preferably 217±2° C. Lazertinib mesylate may have an onset of 214±2° C. Such salts and crystalline forms are described, for example, in WO 2018/194356, which is incorporated by reference herein.

The Lazertinib mesylate may be prepared by a preparation method comprising (a) mixing Lazertinib free-base with a single organic solvent or a mixed solvent, followed by adding methane sulfonic acid thereto to form Lazertinib mesylate, and (b) crystallizing Lazertinib mesylate by adding an organic solvent to the mixture of step (a).

The single organic solvent of step (a) is not particularly limited, but may be selected from the group consisting of acetone, methyl ethyl ketone, and ethyl acetate. The mixed solvent of step (a) may be a mixed solvent of water and one or more suitable organic solvents. Specifically, a mixed solvent of water and one or more organic solvents selected from acetone and methyl ethyl ketone is preferable, but is not limited thereto. A mixing ratio of the water and the organic solvent may be 1:1 to 1:10 in volume ratio and specifically 1:4 to 1:6, but is not limited thereto. The step (a) may be performed at a temperature of 20 to 70° C., preferably 45 to 60° C.

The crystallizing of step (b) may be performed by adding the organic solvent to the mixture obtained in step (a), stirring, cooling, and filtering the mixture, and then drying it to obtain the resulting solid. The organic solvent of step (b) may be the same as or different from the single organic solvent of step (a). Specifically, the organic solvent in step (b) may be at least one selected from the group consisting of acetone, methyl ethyl ketone, and ethyl acetate. The organic solvent in step (b) may be added in volume of 3 mL to 20 mL per 1 g of Lazertinib free-base used in step (a). Specifically, the organic solvent may be added in volume of 5 mL to 20 mL per 1 g of Lazertinib free-base used in step (a) and, more specifically, in volume of 5 mL to 10 mL, but is not limited thereto. The mixture obtained by addition of the organic solvent may be cooled to a temperature of 0 to 30° C., preferably 0 to 10° C., and then dried at a temperature of 30 to 70° C. to isolate Lazertinib mesylate.

The Lazertinib active ingredient may be a provided in the present compositions as a salt, hydrate, or solvate. As noted above, an exemplary salt form is Lazertinib mesylate. WO2018194356 describes the mesylate salt of Lazertinib, and crystalline forms thereof. In the present compositions, crystalline Lazertinib may be a hydrate.

The present compositions may include the active ingredient in a certain weight ratio relative to the combination of diluents. For example, the active ingredient may be present in the pharmaceutical formulation in a weight ratio of 1:1.5 to 1:4 relative to the combination of diluents.

In certain embodiments, the active ingredient is present in the pharmaceutical formulation in a weight ratio of 1:1.6 to 1:4 or in a weight ratio of 1:1.8 to 1:3.9 relative to the combination of diluents.

The active ingredient may be present in an amount of 15-35 wt %, relative to the total weight of the pharmaceutical formulation. In certain embodiments, the active ingredient is present in an amount of 18-35 wt %, relative to the total weight of the pharmaceutical formulation. For example, the active ingredient may be present in an amount of about 18, 19, 20, 21, 22, 23, 24, 25, 26, 27, 28, 29, 30, 31, 32, 33, 34, or 35 wt %, relative to the total weight of the pharmaceutical formulation.

The pharmaceutical composition of the present disclosure may be used for preventing or treating allograft rejection, graft-versus-host disease, diabetic retinopathy, choroidal angiogenesis due to age-related visual loss, psoriasis, arthritis, osteoarthritis, rheumatoid arthritis, pannus invasion of synovial membrane in arthritis, multiple sclerosis, myasthenia gravis, diabetes mellitus, diabetic vascular disease, retinopathy of prematurity, infantile hemangioma, non-small cell lung cancer, bladder cancer, head and neck cancer, prostate cancer, breast cancer, ovarian cancer, gastric cancer, pancreatic cancer, psoriasis, fibrosis, atherosclerosis, recurrent stenosis, autoimmune disease, allergy, respiratory disease, asthma, transplant rejection, inflammation, thrombosis, retinal conduit proliferation, inflammatory bowel disease, Crohn's disease, ulcerative colitis, bone disease, graft or bone marrow transplant rejection, lupus, chronic pancreatitis, cachexia, septic shock, fibrosis and differentiating skin diseases or disorders, central nervous system diseases, neurodegenerative diseases, Alzheimer's disease, Parkinson's disease, disorders or symptoms associated with nerve damage following brain or spinal cord injury and exon metamorphosis, acute or chronic cancer, ocular disease, viral infection, heart disease, lung disease or kidney disease, and bronchitis. The pharmaceutical composition of the present disclosure may be used for the prevention or treatment of preferably acute or chronic cancer, more preferably lung cancer, most preferably non-small cell lung cancer or brain metastatic non-small cell lung cancer, but is not limited thereto.

Hereinafter, the present disclosure will be described in more detail through Examples, which are intended to be illustrative to the present disclosure, although present disclosure is not limited to the Examples.

In the following Examples, "Lazertinib mesylate" refers to the mesylate salt of N-(5-(4-(4-((dimethylamino)methyl)-3-phenyl-1H-pyrazol-1-yl)pirimidine-2-ylamino)-4-methoxy-2-morpholinophenyl)acrylamide.

ENUMERATED EMBODIMENTS

Exemplary numbered embodiments of the present invention are provided below.

1. A pharmaceutical composition for oral administration comprising: N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, or solvate thereof as an active ingredient; and a combination of (i) a cellulose derivative and (ii) a sugar or polyol as diluents, wherein the cellulose derivative and the sugar or polyol are present in the pharmaceutical composition in a weight ratio of 1:0.10 to 1:0.40.

2. The pharmaceutical composition of embodiment 1, wherein the cellulose derivative and the sugar or polyol are present in the pharmaceutical composition in a weight ratio of 1:0.15 to 1:0.40.

3. The pharmaceutical composition of embodiment 1, wherein the cellulose derivative and the sugar or polyol are present in the pharmaceutical composition in a weight ratio of 1:0.20 to 1:0.30.

4. The pharmaceutical composition of embodiment 1, wherein the cellulose derivative and the sugar or polyol are present in the pharmaceutical composition in a weight ratio of 1:0.20 to 1:0.25.

5. The pharmaceutical composition of any one of the preceding embodiments, wherein the cellulose derivative is microcrystalline cellulose.

6. The pharmaceutical composition of any one of the preceding embodiments, wherein the sugar or polyol is mannitol.

7. The pharmaceutical composition of embodiment 1, further comprising: croscarmellose sodium as a disintegrating agent.

8. The pharmaceutical composition of embodiment 7, wherein the croscarmellose sodium is present in a range of 2 to 3 wt %, with respect to the total weight of the composition.

9. The pharmaceutical composition of embodiment 1, further comprising: magnesium stearate as a lubricant.

10. The pharmaceutical composition of embodiment 1, further comprising croscarmellose sodium as a disintegrating agent, and magnesium stearate as a lubricant.

11. The pharmaceutical composition of any preceding embodiment, wherein the active ingredient is N-(5-(4-(4-((dimethylamino)methyl)-3-phenyl-1H-pyrazol-1-yl)pirimidine-2-ylamino)-4-methoxy-2-morpholinophenyl)acrylamide mesylate.

12. The pharmaceutical composition of embodiment 11, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate is a crystalline form having a PXRD pattern with peaks at 5.614, 12.394, 14.086, 17.143, 18.020, 19.104, 21.585, 22.131, and 22.487° 2θ±0.2° 2θ.

13. The pharmaceutical composition of embodiment 11, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate is a crystalline form having a differential scanning calorimeter (DSC) thermogram with an endothermic peak at 210 to 230 QC.

14. The pharmaceutical composition of embodiment 1, wherein the pharmaceutical composition comprises 15-40 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 55-80 wt % of the combination of microcrystalline cellulose and mannitol; 2-3 wt % of croscarmellose sodium; and 0.5 to 2 wt % of magnesium stearate.

15. The pharmaceutical composition of embodiment 1, wherein the pharmaceutical composition comprises 17-38 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 60 to 77 wt % of the combination of microcrystalline cellulose and mannitol; 2.5-3 wt % of croscarmellose sodium; and 0.75-1.25 wt % of magnesium stearate.

16. The pharmaceutical formulation according to any preceding embodiment, further comprising colloidal silicon dioxide.

17. The pharmaceutical formulation according to embodiment 16, wherein the colloidal silicon dioxide is hydrophobic colloidal silicone dioxide.

18. The pharmaceutical formulation according to embodiment 16 or embodiment 17, wherein the colloidal silicone dioxide is present in an amount of about 0.50 wt %, based on the total weight of the pharmaceutical formulation.

19. The pharmaceutical composition of embodiment 15, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate is a crystalline form having a differential scanning calorimeter (DSC) thermogram with an endothermic peak at 217±2 □C.

20. The pharmaceutical formulation according to any preceding embodiment, wherein the active ingredient is present in the pharmaceutical formulation in a weight ratio of 1:1.5 to 1:4 relative to the combination of diluents.

21. The pharmaceutical formulation according to any preceding embodiment, wherein the active ingredient is present in the pharmaceutical formulation in a weight ratio of 1:1.8 to 1:3.9 relative to the combination of diluents.

22. The pharmaceutical formulation according to any preceding embodiment, wherein the active ingredient is present in an amount of 15-35 wt %, relative to the total weight of the pharmaceutical formulation.

23. The pharmaceutical formulation according to any preceding embodiment, wherein the active ingredient is present in an amount of 18-35 wt %, relative to the total weight of the pharmaceutical formulation.

24. The pharmaceutical formulation according to any preceding embodiment, wherein the active ingredient is present in an amount of about 20 wt %, relative to the total weight of the pharmaceutical formulation.

25. The pharmaceutical formulation according to any one of embodiments 1-23, wherein the active ingredient is present in an amount of about 25 wt %, relative to the total weight of the pharmaceutical formulation.

26. A pharmaceutical formulation according to any one of embodiments 1-23 comprising:
lazertinib mesylate (e.g., lazertinib mesylate monohydrate) in an amount equivalent to about 80 mg Lazertinib free base, preferably in an amount of about 95-98 mg, more preferably about 96.48 mg,
microcrystalline cellulose in an amount of about 216-219 mg, more preferably about 218.32 mg,
mannitol in an amount of about 48-52 mg, more preferably about 50 mg, croscarmellose sodium in an amount of about 7-10 mg, more preferably about 9.5 mg,
colloidal silicon dioxide in an amount of about 1-3 mg, more preferably about 1.9 mg, and
magnesium stearate in an amount of about 2-5 mg, more preferably about 3.8 mg.

27. The pharmaceutical formulation according to any one of embodiments 1-23 comprising:
lazertinib mesylate (e.g., lazertinib mesylate monohydrate) in an amount equivalent to about 80 mg Lazertinib free base, preferably in an amount of about 95-98 mg, more preferably 96.48 mg,
microcrystalline cellulose in an amount of about 286-290 mg, more preferably about 288.47 mg,
mannitol in an amount of about 64-68 mg, more preferably about 66 mg, croscarmellose sodium in an amount of about 10-14 mg, more preferably about 12 mg,
colloidal silicon dioxide in an amount of about 1-4 mg, more preferably about 2.35 mg, and
magnesium stearate in an amount of about 3-6 mg, more preferably about 4.7 mg.

28. The pharmaceutical formulation according to any one of embodiments 1-23 comprising:
lazertinib mesylate (e.g., lazertinib mesylate monohydrate) in an amount equivalent to about 240 mg Lazertinib free base, preferably in an amount of about 287-291 mg, more preferably about 289.44 mg,
microcrystalline cellulose in an amount of about 652-656 mg, more preferably about 654.96 mg,
mannitol in an amount of about 148-152 mg, more preferably about 150 mg, croscarmellose sodium in an amount of about 26-30 mg, more preferably about 28.5 mg,
colloidal silicon dioxide in an amount of about 4-7 mg, more preferably about 5.7 mg, and
magnesium stearate in an amount of about 9-13 mg, more preferably about 11.4 mg.

29. The pharmaceutical formulation according to any one of embodiments 26-28, wherein the Lazertinib mesylate (e.g., Lazertinib mesylate monohydrate) is a crystalline form having diffraction peaks in a PXRD (powder X-ray diffraction) graph present at 2θ (theta) angles of 5.614±0.2, 12.394±0.2, 14.086±0.2, 17.143±0.2, 18.020±0.2, 19.104±0.2, 21.585±0.2, 22.131±0.2, and 22.487±0.2 degrees.

30. The pharmaceutical formulation according to any one of embodiments 26-29, wherein the Lazertinib mesylate (e.g., Lazertinib mesylate monohydrate) is a crystalline form having a PXRD pattern with peaks at 5.614, 12.394, 14.086, 17.143, 18.020, 19.104, 21.585, 22.131, and 22.487° 2θ±0.2° 2θ.

31. The pharmaceutical formulation according to any one of embodiments 26-30, wherein the Lazertinib mesylate (e.g., Lazertinib mesylate monohydrate) is a crystalline form having a differential scanning calorimeter (DSC) thermogram with an endothermic peak at 210 to 230° C., preferably 217±2° C.

32. The pharmaceutical formulation according to any one of embodiments 26-31 in the form of a tablet, wherein the tablet optionally further includes a coating material.

33A. A method of treating cancer in a patient comprising administering to the patient a pharmaceutical formulation according to any of embodiments 1-32.

33B. A pharmaceutical formulation according to any of embodiments 1-32 for use in the treatment of cancer (e.g., lung cancer, such as non-small cell lung cancer).

33C. Use of a pharmaceutical formulation according to any of embodiments 1-32 for the manufacture of a medicament for the treatment of cancer (e.g., lung cancer, such as non-small cell lung cancer).

34. A method or use according to any of embodiments 33A, 33B or 33C, wherein the patient has been diagnosed with lung cancer.

35. A method or use according to any of embodiments 33A, 33B or 33C, wherein the patient has been diagnosed with non-small cell lung-cancer.

36. A method or use according to any of embodiments 33A, 33B or 33C, wherein the patient has been diagnosed with epidermal growth factor receptor mutation positive (EGFRm+) advanced non-small cell lung cancer.

37. A method or use according to any of embodiments 33A, 33B or 33C, or 34-36, wherein the patient has had progressive disease on prior epidermal growth factor receptor tyrosine kinase inhibitor (EGFR-TKI) therapy.

38. A method or use according to any of embodiments 33A, 33B or 33C, or 34-37 wherein the patient has one or more EGFR mutations; for example, an EGFR T790M mutation.

39. A method or use according to any of embodiments 33A, 33B or 33C, or 34-38, comprising administering the pharmaceutical formulation daily.

40. A method or use according to any of embodiments 33A, 33B or 33C, or 34-38, comprising administering the pharmaceutical formulation once daily.

41. A method or use according to any of embodiments 33A, 33B or 33C, or 34-40, comprising administering the pharmaceutical formulation in an amount that provides about 240 mg lazertinib free base per day (e.g., by administering three tablets per day wherein each tablet contains an equivalent of about 80 mg Lazertinib free base, or by administering one tablet per day wherein the tablet contains an equivalent of about 240 mg Lazertinib free base).

42. A method or use according to any of embodiments 33A, 33B or 33C, or 34-40, comprising administering the pharmaceutical formulation in an amount that provides about 80 mg lazertinib free base per day (e.g., by administering one tablet per day wherein the tablet contains an equivalent of about 80 mg Lazertinib free base).

43. A method or use according to any of embodiments 33A, 33B or 33C, or 34-40, comprising administering the pharmaceutical formulation in an amount that provides about 160 mg lazertinib free base per day (e.g., by administering two tablets per day wherein each tablet contains an equivalent of about 80 mg Lazertinib free base).

44. A method or use according to any of embodiments 33A, 33B or 33C, or 34-40, comprising administering the pharmaceutical formulation in an amount that provides about 320 mg lazertinib free base per day (e.g., by administering four tablets per day wherein each tablet contains an equivalent of about 80 mg Lazertinib free base, or by administering two tablets per day wherein one tablet contains an equivalent of about 240 mg Lazertinib free base and one tablet contains an equivalent of about 80 mg Lazertinib free base).

45. A method or use according to any of embodiments 33A, 33B or 33C, or 34-44, comprising administering the pharmaceutical formulation as part of a combination regimen with one or more additional anti-cancer agents.

46. The method or use according to embodiment 45, wherein the one or more additional anti-cancer agents include a bispecific anti-EGFR/c-Met antibody.

47. The method or use according to embodiment 46, wherein the bispecific anti-EGFR/c-Met antibody is JNJ-61186372 (JNJ-372) (as described in U.S. Pat. No. 9,593,164, and U.S. Publication No. 2020/0360394, which are incorporated by reference herein).

EXAMPLES

Example 1—Preparation of Pharmaceutical Compositions and Compression Testing

Preparation of comparative composition. Previously developed dosage forms were manufactured and subjected to compression studies in order to assess manufacturability relative to pharmaceutical compositions according to the present disclosure.

The formula for the comparative composition is shown in Table 1, below. A core tablet, as used herein, preferably refers to a tablet without a coating material. A coated tablet, as used herein, preferably refers to a tablet that includes a core tablet and also a coating material.

TABLE 1

| Components | Mg/tab | % w/w |
|---|---|---|
| Lazertinib mesylate [1] | 93.86 [1] | 39.94 |
| Microcrystalline cellulose (Vivapur 112) | 67.14 | 28.57 |
| Mannitol (Pearlitol 200SD) | 66.00 | 28.09 |
| Croscarmellose sodium (Ac-DI-Sol) | 6.00 | 2.55 |
| Magnesium stearate (MF-2-V Vegetable) | 2.00 | 0.85 |
| Opadry AMB80W62680 | 7.05 | 3.00 |
| Core tablet | 235.00 | 100.00 |
| Coated tablet | 242.05 | 103.00 |

[1] 80 mg of lazertinib per tablet is equivalent to 93.86 mg of lazertinib mesylate The manufacturing process for the comparative composition was as follows:
i. The weighed qty. per batch of lazertinib mesylate was passed through a #20 mesh screen and transferred to a bin.
ii. The weighed qty. of microcrystalline cellulose (Vivapur 112) was added to the step i. and the materials were blended for a defined number of revolutions using a suitable blender.
iii. The weighed qty. of mannitol and croscarmellose sodium were added to the blend of step ii. and the combination was blended for a defined number of revolutions using a suitable blender.
iv. The magnesium stearate was passed through a suitable screen and added to the blend of step iii.
v. The materials of step iv. were blended for a defined number of revolutions using a suitable blender.
vi. The blend of step v. was compressed using a rotary compression machine and suitable tablet tools into tablets with average weight of 235 mg.
vii. Opadry amb 80W62680 coating material was dispersed in a vortex of purified water using a suitable container equipped with a mixer. Mixed for a defined time period and until no lumps are present.
viii. The core tablets of step vi. were film coated using the coating suspension of step vii. in a perforated film coating equipment to a predefined weight gain.
ix. Film-coated tablets were unloaded and packed appropriately.

Compression testing of comparative composition. Compression studies were executed on certain batches of the comparative composition. Compression was executed using a power assisted rotary tablet press. Typically, process parameters such as precompression force, compression force and compression speed may have an impact on tablet in-process controls such as hardness, thickness, disintegration time and friability. Therefore, the outcome of the compression studies confirms if the process is robust and can assure a comfortable range of acceptable In Process Controls (IPCs) towards scale up and commercial manufacturability. Samples of tablets were collected at each challenged compression study profile run and evaluated for the above mentioned IPCs.

The following IPC test methods were used to assess tablet properties:
A. Appearance: Visual Inspection
B. Weight: Weight measurement, the weight of tablets is measured using an analytical balance
C. Thickness: thickness measurement, the thickness of tablets is measured using an micrometer.
D. Hardness: Hardness measurement: A tablet is placed between anvils (or two platens, one of which moves to apply sufficient force to the tablet to cause fracture), and the crushing strength that just causes the tablet to break is recorded.
E. Friability: Ph.Eur. 2.9.7/USP test <1216>: for tablets with a unit weight equal to or less than 650 mg, take a sample of whole tablets corresponding as near as possible to 6.5 g. For tablets with a unit weight of more than 650 mg, take a sample of 10 whole tablets. The tablets should be carefully dedusted prior to testing. Accurately weigh the tablet sample and place the tablets in the drum. Rotate the drum 100 times, and remove the tablets. Remove any loose dust from the tablets as before and accurately weigh them. Generally, the test is run once. If obviously cracked, cleaved, or broken tablets are present in the tablet sample after tumbling, the sample fails the test. If the results are difficult to interpret or if the weight loss is greater than the targeted value, the test should be repeated twice and the mean of the three tests determined. A maximum mean weight loss from the three samples of not more than 1.0% is considered acceptable for most products.
F. Disintegration test: This test is to determine whether a tablet disintegrates within the prescribed time when placed in a liquid medium at experimental conditions.

Place 1 dosage unit in each of the six tubes of the basket and if required add a disk. Operate the apparatus using water maintained at 37° C.±2° C. Record the time for complete disintegration of the tablets.

Provided below in Tables 2 and 3 are experimental examples for the performance of the comparative composition linked to the core tablet IPCs during compression studies.

TABLE 2

Compression Experiments

| Exp. Run Order | Compression speed (rpm) | Compression force (kN) | Pre-compression force (kN) | Hardness (kp) (n = 5) | Thickness (mm) (n = 5) | Weight (mg) (n = 10) | Friability (%) (NLT 6.5 g) | Disintegration time (mins) (n = 6) |
|---|---|---|---|---|---|---|---|---|
| 1 | 30 | 4.6  | 1.4 | 2.5-3.2 | 4.46-4.47 | 232-239 | 0.00 | 0.27-0.29 |
| 2 | 30 | 8.3  | 1.0 | 5.4-6.5 | 4.24-4.28 | 231-239 | 0.00 | 0.24-0.27 |
| 3 | 30 | 11.1 | 1.2 | 6.4-7.3 | 4.21-4.28 | 236-242 | 0.04 | 0.42-0.44 |
| 4 | 30 | 14.7 | 1.2 | 7.5-8.2 | 4.14-4.17 | 236-244 | 0.03 | 1.12-1.14 |
| 5 | 30 | 16.2 | 1.1 | 6.5-8.9 | 4.12-4.17 | 237-243 | 0.00 | 1.07-1.09 |
| 6 | 45 | 15.8 | 1.0 | 5.7-7.7 | 4.09-4.17 | 232-239 | 0.00 | 0.53-0.55 |
| 7 | 60 | 15.7 | 1.0 | 5.4-8.0 | 4.09-4.15 | 230-243 | 0.00 | 0.49-0.52 |
| 8 | 30 | 16.1 | 1.0 | 7.4-7.9 | 4.06-4.14 | 234-240 | 0.00 | 0.55-0.57 |
| 9 | 60 | 16.0 | 1.0 | 7.4-7.7 | 4.09-4.12 | 235-241 | 0.00 | 0.50-0.52 |

TABLE 3

Additional Compression Experiments

| Exp. Run order | Compression speed (rpm) | Compression force (kN) | Pre-compression force (kN) | Hardness (kp) (n = 10) | Thickness (mm) (n = 10) | Weight (mg) (n = 10) | Friability (%) (NLT 6.5 g) | Disintegration time (min) (n = 6) |
|---|---|---|---|---|---|---|---|---|
| 1 | 30 | 11.3 | 1.0 | 8.0-9.7  | 4.16-4.21 | 233-241 | 0.00 | 0.32-0.38 |
| 2 | 30 | 8.3  | 1.0 | 6.1-7.0  | 4.28-4.30 | 235-242 | 0.00 | 1.00-1.08 |
| 3 | 30 | 14.2 | 1.0 | 9.1-10.4 | 4.12-4.16 | 234-242 | 0.00 | 0.25-0.32 |

Preparation of inventive compositions. Exemplary compositions according to the present disclosure were prepared from materials as provided in Table 4, below.

TABLE 4

| Component | Mg/tab | % w/w |
|---|---|---|
| Lazertinib mesylate [1] | 93.86 [1] | 19.97 |
| Microcrystalline cellulose (Vivapur 112) | 67.29 | 14.32 |
| Microcrystalline cellulose (Avicel PH 102) | 223.80 | 47.62 |
| Mannitol (Pearlitol 200SD) | 66.00 | 14.04 |
| Croscarmellose sodium (Ac-DI-Sol) | 12.00 | 2.55 |
| Silica hydrophobic colloidal (Aerosil R972) | 2.35 | 0.50 |
| Magnesium stearate (MF-2-V Vegetable) | 4.70 | 1.00 |
| Core tablet | 470.00 | 100.00 |
| Opadry AMB80W62680 | 14.10 | 3.00 |
| Coated tablet | 484.10 | — |

[1] 80 mg of lazertinib per tablet is equivalent to 93.86 mg of lazertinib mesylate The manufacturing process for the inventive compositions was as follows:
i. The weighed qty. per batch of lazertinib mesylate and Aerosil R972 were passed through a suitable screen, transferred to a bin and blended for a defined number of revolutions using a suitable blender.
ii. The weighed qty. of mannitol, microcrystalline cellulose and croscarmellose sodium were added to the blend of step i. and blend for a defined number of revolutions using a suitable blender.
iii. The magnesium stearate was passed through a suitable screen and add to the blend of step ii.
iv. The materials of step iii. were blended for a defined number of revolutions using a suitable blender.
v. The blend of step iv. was compressed using a rotary compression machine and suitable tablet tools into tablets with average weight of 470 mg.
vi. Opadry amb 80W62680 coating material was dispersed in a vortex of purified water using a suitable container equipped with a mixer. Mixed for a defined time period and until no lumps were present.
vii. The core tablets of step v. were film coated using the coating suspension of step vi. in a perforated film coating equipment to a predefined weight gain.
viii. The film-coated tablets were unloaded and packed appropriately.

An alternative manufacturing process for the inventive compositions is as follows:
i. The weighed qty. per batch of lazertinib mesylate, Aerosil R972, mannitol, microcrystalline cellulose and croscarmellose sodium are passed through a suitable screen, transferred to a bin and blended for a defined number of revolutions using a suitable blender.
ii. Pass the magnesium stearate through a suitable screen and add to the blend of step ii.
iii. Blend the materials of step iii. for a defined number of revolutions using a suitable blender.
iv. Compress the blend of step iv. using a rotary compression machine and suitable tablet tools into tablets with average weight of 470 mg.
v. Disperse Opadry amb 80W62680 coating material in a vortex of purified water using a suitable container equipped with a mixer. Mix for a defined time period and until no lumps are present.
vi. Film coat the core tables of step v. using the coating suspension of step vi. in a perforated film coating equipment to a predefined weight gain.
vii. Unload the film coated tablets and pack them appropriately.

Compression testing of inventive compositions. Compression studies were executed on some batches of the inventive formulation. The compression was executed using a power assisted rotary tablet press. Typically, process parameters such as precompression force, compression force and compression speed may have an impact on tablet in-process controls such as hardness, thickness, disintegration time and friability. Therefore, the outcome of the compression studies confirmed if the process was robust and can assure a comfortable range of acceptable In Process Controls (IPCs) towards scale up and commercial manufacturability. Samples of tablets were collected at each challenged compression study profile run and evaluated for the above mentioned IPCs.

The following test methods have been used to assess the In-process tablet properties:

A. Appearance: Visual Inspection
B. Weight: Weight measurement, the weight of tablets is measured using an analytical balance
C. Thickness: thickness measurement, the thickness of tablets is measured using an micrometer.
D. Hardness: Hardness measurement: A tablet is placed between anvils (or two platens, one of which moves to apply sufficient force to the tablet to cause fracture), and the crushing strength that just causes the tablet to break is recorded.
E. Friability: Ph.Eur. 2.9.7/USP test <1216>: for tablets with a unit weight equal to or less than 650 mg, take a sample of whole tablets corresponding as near as possible to 6.5 g. For tablets with a unit weight of more than 650 mg, take a sample of 10 whole tablets. The tablets should be carefully dedusted prior to testing. Accurately weigh the tablet sample and place the tablets in the drum. Rotate the drum 100 times, and remove the tablets. Remove any loose dust from the tablets as before and accurately weigh them. Generally, the test is run once. If obviously cracked, cleaved, or broken tablets are present in the tablet sample after tumbling, the sample fails the test. If the results are difficult to interpret or if the weight loss is greater than the targeted value, the test should be repeated twice and the mean of the three tests determined. A maximum mean weight loss from the three samples of not more than 1.0% is considered acceptable for most products.

G. Disintegration time of tablets: Disintegration test: This test is to determine whether a tablet disintegrates within the prescribed time when placed in a liquid medium at experimental conditions. Place 1 dosage unit in each of the six tubes of the basket and if required add a disk. Operate the apparatus using water maintained at 37° C.±2° C. Record the time for complete disintegration of the tablets.

Provided below in Tables 5-7 are respective experimental examples for the performance of the tested inventive compositions linked to the core tablet IPCs during compression studies. All of the tested compositions were in accordance with the contents of Table 4.

TABLE 5

| Exp. Run order | Compression speed (rpm) | Compression force (kN) | Pre-compression force (kN) | Hardness (kp) (n = 5) | Thickness (mm) (n = 5) | Weight (mg) (n = 10) | Friability (%) (NLT 6.5 g) | Disintegration time (min) (n = 6) |
|---|---|---|---|---|---|---|---|---|
| 1 | 30 | 8.2  | 1.2 | 13.0-14.3 | 5.52-5.59 | 468-473 | 0.12 | 0.27-0.29 |
| 2 | 30 | 10.8 | 1.1 | 17.1-18.0 | 5.31-5.35 | 469-474 | 0.00 | 0.36-0.38 |
| 3 | 30 | 14.3 | 1.1 | 21.1-23.1 | 5.12-5.17 | 468-471 | 0.00 | 0.49-0.52 |
| 4 | 30 | 17.3 | 1.1 | 24.0.-27.1 | 5.04-5.09 | 469-474 | 0.00 | 1.50-1.54 |

TABLE 6

| Exp. Run order | Compression speed (rpm) | Compression force (kN) | Pre-compression force (kN) | Hardness (kp) (n = 10) | Thickness (mm) (n = 10) | Weight (mg) (n = 10) | Friability (%) (NLT 6.5 g) | Disintegration time (min) (N = 6) |
|---|---|---|---|---|---|---|---|---|
| 1 | 30 | 12.1 | 1.1 | 21.6-23.5 | 5.19-5.22 | 467-472 | 0.17 | 0.50-0.56 |
| 2 | 30 | 8.9  | 1.2 | 15.9-17.6 | 5.40-5.44 | 469-474 | 0.02 | 0.19-0.26 |
| 3 | 30 | 15.0 | 1.2 | 26.1-28.0 | 5.08-5.14 | 468-473 | 0.00 | 0.48-1.05 |

TABLE 7

| Exp. Run order | Compression speed (rpm) | Compression force (kN) | Pre-compression force (kN) | Hardness (kp) | Thickness (mm) | Weight (mg) | Friability (%) | Disintegration time (min) (N = 6) |
|---|---|---|---|---|---|---|---|---|
| 1 | 15 | 13.5 | 2.0 | 20.8-24.8 | 5.19-5.21 | 469-472 | 0.00 | 0.38 |
| 2 | 15 | 10.6 | 1.0 | 12.8-18.1 | 5.37-5.40 | 470-474 | 0.00 | 0.16 |
| 3 | 15 | 16.5 | 2.0 | 22.4-27.2 | 5.11-5.13 | 468-474 | 0.03 | 0.39 |

FIG. 1 illustrates a comparison between the comparative formulation and the formulation according to the present disclosure with respect to measured compression force vs. tablet hardness. The prior art comparative formulation displayed a very narrow compression force to hardness profile window between 3 to 9 kp of average tablet hardness for a compression force ranging between 5 to 16 kN. For a similar compression force range between 8 to 17 kN, the inventive formulation displayed a wide hardness profile window between 14 to 25 kp of average tablet hardness.

Examples 2-11—Preparation and Compression Testing of Additional Inventive Compositions Example 2

Using the manufacturing and compression testing procedures described for the inventive compositions in Example 1 (in particular, the "alternative manufacturing process" was used), a further inventive composition representing a 80 mg lazertinib tablet was prepared and tested. Table 8 lists the components and their amounts within the tablet, and Table 9 provides the results of compression testing of the composition prepared from a medium scale batch (~14.6 kg).

TABLE 8

| Components | Mg/tablet | % w/w |
|---|---|---|
| Lazertinib mesylate[1] | 93.86[1] | 19.97 |
| Microcrystalline cellulose (Vivapur 112) | 67.29 | 14.32 |
| Microcrystalline cellulose (Avicel PH 102) | 223.8 | 47.62 |
| Mannitol (pearlitol SD 200) | 66.0 | 14.04 |
| Croscarmellose sodium (Ac-di-sol) | 12.0 | 2.55 |
| Silica hydrophobic colloidal (Aerosil R972) | 2.35 | 0.5 |
| Magnesium stearate | 4.7 | 1.0 |
| Av. Weight of core tablet | 470.0 | 100 |

[1]80 mg of lazertinib per tablet is equivalent to 93.86 mg of lazertinib mesylate

TABLE 9

| Compression force (kN) | Pre-compression force (kN) | Hardness (N) | Thickness (mm) | Weight (mg) | Friability (%) | Disintegration time (min) (N = 6) |
|---|---|---|---|---|---|---|
| 4.09 | 1.0 | 71-81 | 5.60-5.64 | 467-472 | 0 | 0.27 |
| 7.95 | 1.0 | 158-179 | 5.03-5.07 | 467-474 | NT | 0.17 |
| 12.00 | 1.0 | 209-233 | 4.81-4.83 | 466-473 | 0 | 0.57 |
| 16.38 | 1.0 | 268-296 | 4.63-4.66 | 465-475 | NT | 1.27 |
| 20.03 | 1.0 | 309-338 | 4.56-4.59 | 468-476 | NT | 2.05 |

NT = Not tested

Figure 2:
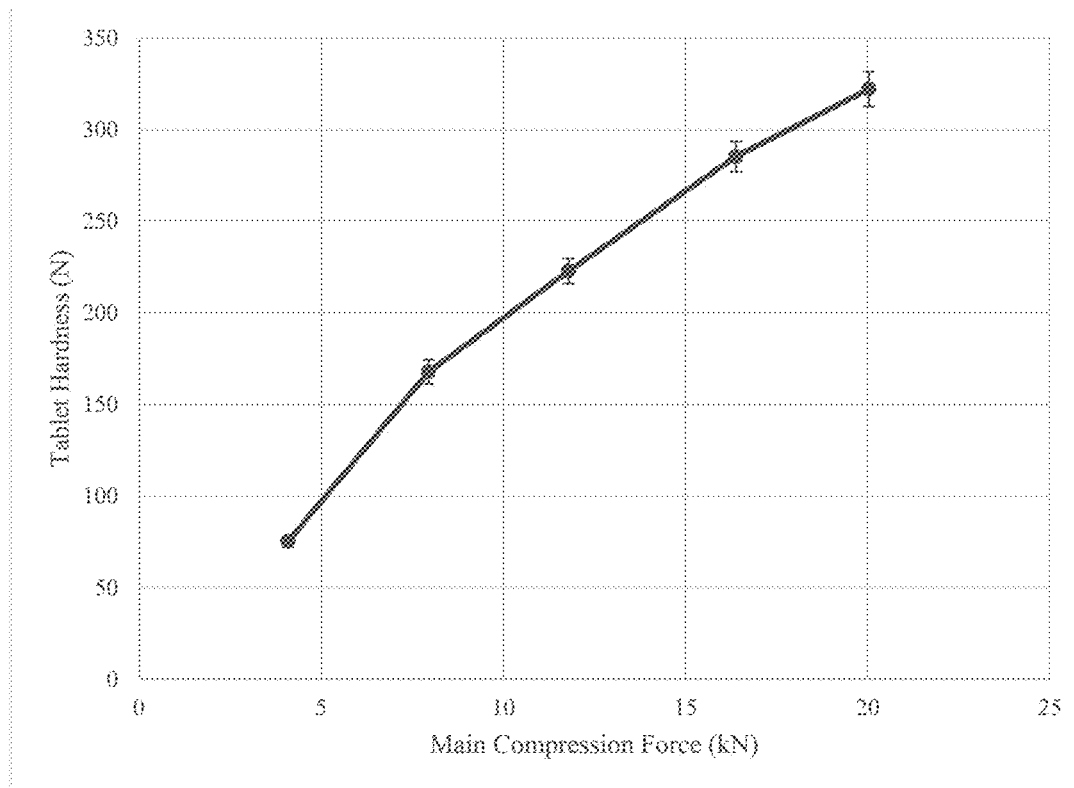
FIG. 2 illustrates the results of a compression force profile study of a composition according to the present disclosure.

FIG. 2 illustrates the results of a compression force profile study of the composition according to Table 8.

Example 3

Using the manufacturing and compression testing procedures described for the inventive compositions in Example 1, a further inventive composition representing a 80 mg lazertinib tablet was prepared and tested. Table 10 lists the components and their amounts within the tablet, and Table 11 provides the results of compression testing of the composition.

TABLE 10

| Components | Mg/tablet | % w/w |
|---|---|---|
| Lazertinib mesylate[1] | 93.86[1] | 19.97 |
| Microcrystalline cellulose (Vivapur 112) | 67.29 | 14.32 |
| Microcrystalline cellulose (Avicel PH 102) | 226.15 | 48.12 |
| Mannitol (pearlitol SD 200) | 66.0 | 14.04 |
| Croscarmellose sodium (Ac-di-sol) | 12.0 | 2.55 |
| Magnesium stearate | 4.7 | 1.0 |
| Av. Weight of core tablet | 470.0 | 100 |

[1]80 mg of lazertinib per tablet is equivalent to 93.86 mg of lazertinib mesylate

TABLE 11

| Compression force (kN) | Pre-compression force (kN) | Hardness (N) | Thickness (mm) | Weight (mg) | Disintegration time (min)* |
|---|---|---|---|---|---|
| 10 | 1.0 | 150-159 | 4.93-4.96 | 475-476 | 0.23 |
| 15 | 1.0 | 201-227 | 4.60-4.71 | 469-473 | 0.57 |
| 20 | 1.0 | 251-263 | 4.51-4.54 | 475-477 | 1.25 |

*n = 6 for compression force 15 kN. n = 3 for compression forces 10 and 20 kN

Figure 3:
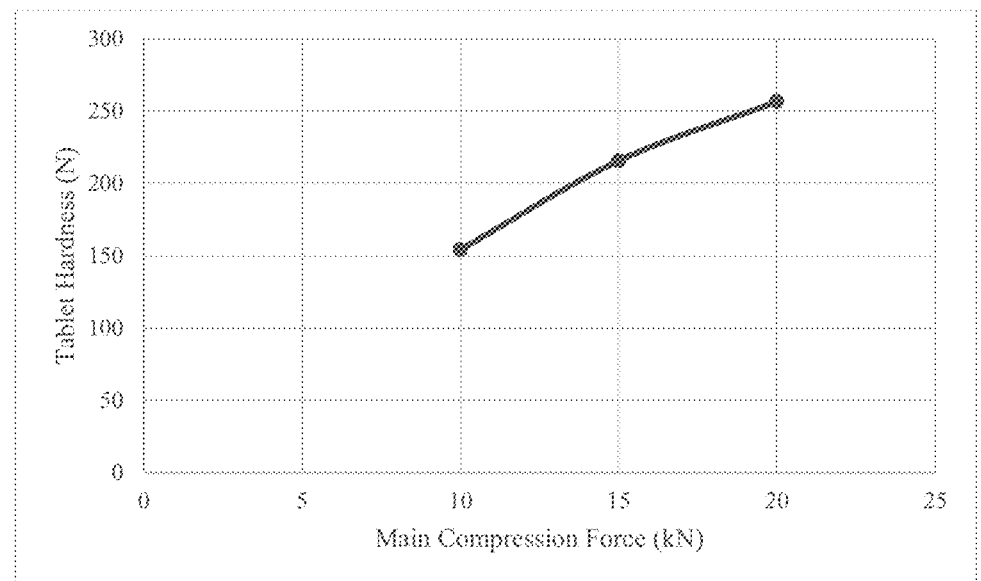
FIG. 3 illustrates the results of a compression force profile study of a further composition according to the present disclosure.

FIG. 3 illustrates the results of a compression force profile study of the composition according to Table 10.

Example 4

Using the manufacturing and compression testing procedures described for the inventive compositions in Example 1, a further inventive composition representing a further 80 mg lazertinib tablet was prepared and tested. Table 12 lists the components and their amounts within the tablet, and Table 13 provides the results of compression testing of the composition.

TABLE 12

| Components | Mg/tablet | % w/w |
|---|---|---|
| Lazertinib mesylate[1] | 93.86[1] | 19.97 |
| Microcrystalline cellulose (Avicel PH 102) | 291.09 | 61.93 |
| Mannitol (pearlitol SD 200) | 66.0 | 14.04 |
| Croscarmellose sodium (Ac-di-sol) | 12.0 | 2.55 |

TABLE 12-continued

| Components | Mg/tablet | % w/w |
|---|---|---|
| Silica hydrophobic colloidal (Aerosil R972) | 2.35 | 0.5 |
| Magnesium stearate | 4.7 | 1.0 |
| Av. Weight of core tablet | 470.0 | 100 |

[1]80 mg of lazertinib per tablet is equivalent to 93.86 mg of lazertinib mesylate

TABLE 13

| Compression force (kN) | Pre-compression force (kN) | Hardness (N) | Thickness (mm) | Weight (mg) | Disintegration time (min)* |
|---|---|---|---|---|---|
| 9 | 1.0 | 167-173 | 4.95-5.03 | 471-473 | 0.25 |
| 11 | 1.0 | 207-231 | 4.72-4.95 | 468-474 | 0.5 |
| 15 | 1.0 | 267-273 | 4.60-4.63 | 471-472 | 0.9 |

*n = 6 for compression force 11 kN. n = 3 for compression forces 9 and 15 kN

Figure 4:
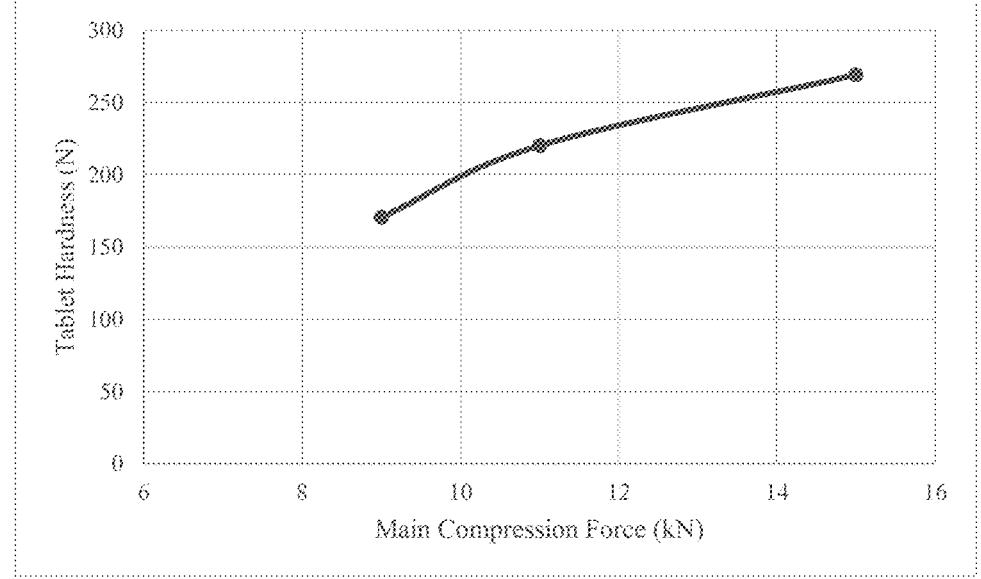
FIG. 4 illustrates the results of a compression force profile study of a further composition according to the present disclosure.

FIG. 4 illustrates the results of a compression force profile study of the composition according to Table 12.

Example 5

Using the manufacturing and compression testing procedures described for the inventive compositions in Example 1, a further inventive composition representing a further 80 mg lazertinib tablet was prepared and tested. Table 14 lists the components and their amounts within the tablet, and Table 15 provides the results of compression testing of the composition.

TABLE 14

| Components | Mg/tablet | % w/w |
|---|---|---|
| Lazertinib mesylate[1] | 93.86[1] | 24.70 |
| Microcrystalline cellulose (Avicel PH 102) | 220.94 | 58.14 |
| Mannitol (pearlitol SD 200) | 50.0 | 13.16 |
| Croscarmellose sodium (Ac-di-sol) | 9.5 | 2.5 |
| Silica hydrophobic colloidal (Aerosil R972) | 1.9 | 0.5 |
| Magnesium stearate | 3.8 | 1.0 |
| Av. Weight of core tablet | 380.0 | 100 |

[1]80 mg of lazertinib per tablet is equivalent to 93.86 mg of lazertinib mesylate

TABLE 15

| Compression force (kN) | Pre-compression force (kN) | Hardness (N) | Thickness (mm) | Weight (mg) | Disintegration time (min) |
|---|---|---|---|---|---|
| 5 | 1.0 | 92-95 | 5.35-5.42 | 377-380 | 0.15 |
| 7.5 | 1.0 | 142-173 | 4.89-4.96 | 376-381 | 0.27 |
| 10 | 1.0 | 216-227 | 4.69-4.70 | 378-380 | 0.57 |

Figure 5:
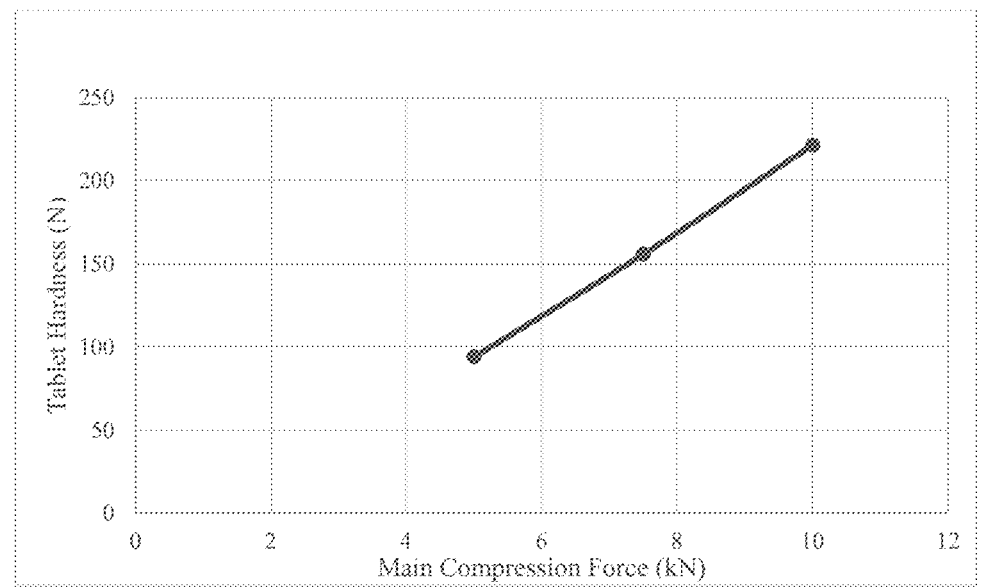
FIG. 5 illustrates the results of a compression force profile study of a further composition according to the present disclosure.

*n = 6 for compression force 7.5 kN. n = 3 for compression forces 5.0 and 10.0 kN FIG. 5 illustrates the results of a compression force profile study of the composition according to Table 14.

Example 6

Using the manufacturing and compression testing procedures described for the inventive compositions in Example 1, a further inventive composition representing a further 80 mg lazertinib tablet was prepared and tested. Table 16 lists the components and their amounts within the tablet, and Table 17 provides the results of compression testing of the composition.

TABLE 16

| Components | Mg/tablet | % w/w |
|---|---|---|
| Lazertinib mesylate[1] | 93.86[1] | 24.70 |
| Microcrystalline cellulose (Avicel PH 102) | 222.84 | 58.64 |
| Mannitol (pearlitol SD 200) | 50.0 | 13.16 |
| Croscarmellose sodium (Ac-di-sol) | 9.5 | 2.5 |
| Magnesium stearate | 3.8 | 1.0 |
| Av. Weight of core tablet | 380.0 | 100 |

[1]80 mg of lazertinib per tablet is equivalent to 93.86 mg of lazertinib mesylate

TABLE 17

| Compression force (kN) | Pre-compression force (kN) | Hardness (N) | Thickness (mm) | Weight (mg) | Disintegration time (min)* |
|---|---|---|---|---|---|
| 9 | 1.0 | 131-139 | 4.79-4.84 | 384-388 | 0.3 |
| 13 | 1.0 | 169-174 | 4.64-4.67 | 383-385 | 0.52 |
| 15 | 1.0 | 196-205 | 4.51-4.54 | 385-387 | 1.23 |

*n = 6 for compression force 13 kN. n = 3 for compression forces 9 and 15 kN

Figure 6:
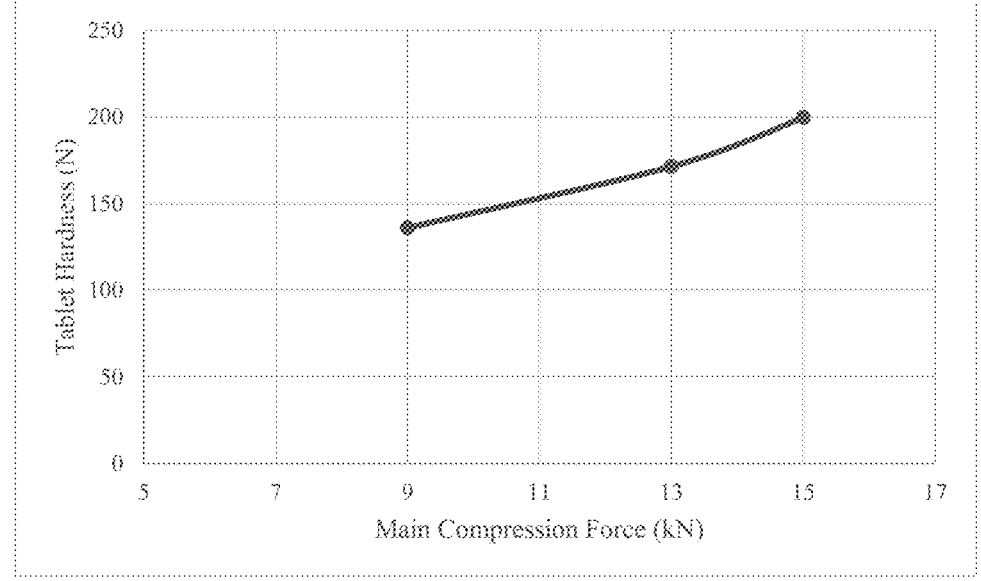
FIG. 6 illustrates the results of a compression force profile study of a further composition according to the present disclosure.

FIG. 6 illustrates the results of a compression force profile study of the composition according to Table 16.

Example 7

Using the manufacturing and compression testing procedures described for the inventive compositions in Example 1, a further inventive composition representing a further 80 mg lazertinib tablet was prepared and tested. Table 18 lists the components and their amounts within the tablet, and Table 19 provides the results of compression testing of the composition.

TABLE 18

| Components | Mg/tablet | % w/w |
|---|---|---|
| Lazertinib mesylate[1] | 93.86[1] | 34.13 |
| Microcrystalline cellulose (Avicel PH 102) | 139.44 | 50.71 |
| Mannitol (pearlitol SD 200) | 32 | 11.64 |
| Croscarmellose sodium (Ac-di-sol) | 6.9 | 2.51 |
| Magnesium stearate | 2.8 | 1.02 |
| Av. Weight of core tablet | 275.0 | 100 |

[1]80 mg of lazertinib per tablet is equivalent to 93.86 mg of lazertinib mesylate

TABLE 19

| Compression force (kN) | Pre-compression force (kN) | Hardness (N) | Thickness (mm) | Weight (mg) | Disintegration time (min)* |
|---|---|---|---|---|---|
| 10 | 1.0 | 97-104 | 3.84-3.87 | 276-277 | NT |
| 20 | 1.0 | 102-114 | 3.77-3.8 | 277-279 | NT |
| 30 | 1.0 | 111-121 | 3.71-3.79 | 277-281 | NT |

TABLE 19-continued

| Compression force (kN) | Pre-compression force (kN) | Hardness (N) | Thickness (mm) | Weight (mg) | Disintegration time (min)* |
|---|---|---|---|---|---|

*NT = Not tested

Figure 7:
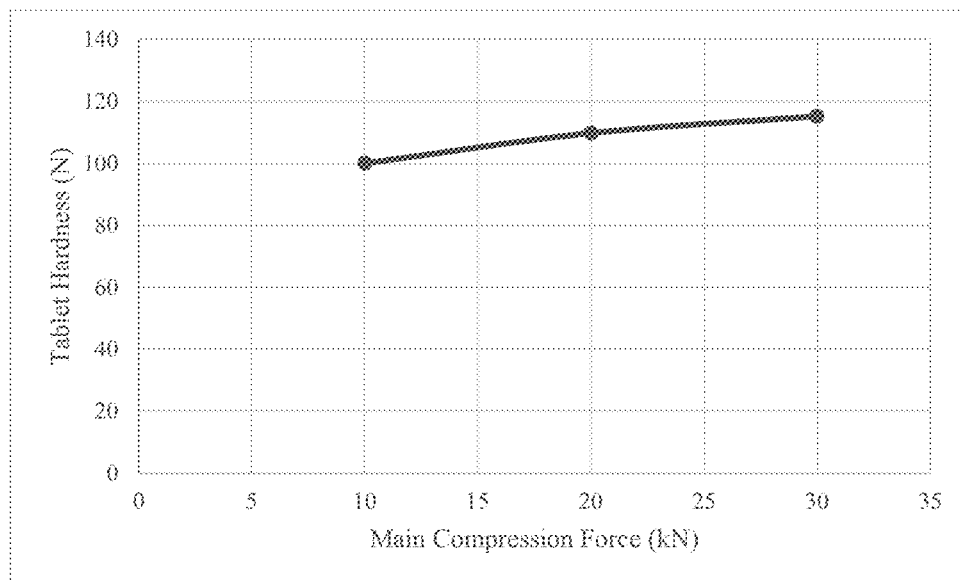
FIG. 7 illustrates the results of a compression force profile study of a further composition according to the present disclosure.

FIG. 7 illustrates the results of a compression force profile study of the composition according to Table 18.

Example 8

Using the manufacturing and compression testing procedures described for the inventive compositions in Example 1, a further inventive composition representing a 160 mg lazertinib tablet was prepared and tested. Table 20 lists the components and their amounts within the tablet, and Table 21 provides the proposed results of compression testing of the composition, i.e., compression is expressed as target conditions only—no compression profile was generated at this scale.

TABLE 20

| Components | Mg/tablet | % w/w |
|---|---|---|
| Lazertinib mesylate[1] | 187.72[1] | 24.70 |
| Microcrystalline cellulose (Avicel PH 102) | 445.68 | 58.64 |
| Mannitol (pearlitol SD 200) | 100 | 13.16 |
| Croscarmellose sodium (Ac-di-sol) | 19 | 2.5 |
| Magnesium stearate | 7.6 | 1.0 |
| Av. Weight of core tablet | 760.0 | 100 |

[1]160 mg of lazertinib per tablet is equivalent to 187.72 mg of lazertinib mesylate

TABLE 21

| Compression force (kN) | Pre-compression force (kN) | Hardness (N) | Thickness (mm) | Weight (mg) | Disintegration time (min)* |
|---|---|---|---|---|---|
| N/A | 1.0 | 198-220 | 6.26-6.45 | 759-766 | 0.28 |

Example 9

Using the manufacturing and compression testing procedures described for the inventive compositions in Example 1 (in particular, the "alternative manufacturing process" was used), a further inventive composition representing a 240 mg lazertinib tablet was prepared and tested. Table 22 lists the components and their amounts within the tablet, and Table 23 provides the results of compression testing of the composition prepared from a medium scale batch (~20 kg).

TABLE 22

| Components | Mg/tablet | % w/w |
|---|---|---|
| Lazertinib mesylate[1] | 281.58[1] | 24.70 |
| Microcrystalline cellulose (Avicel PH 102) | 668.52 | 58.64 |
| Mannitol (pearlitol SD 200) | 150.0 | 13.16 |
| Croscarmellose sodium (Ac-di-sol) | 28.5 | 2.5 |
| Magnesium stearate | 11.4 | 1.0 |
| Av. Weight of core tablet | 1140 | 100 |

[1]240 mg of lazertinib per tablet is equivalent to 281.58 mg of lazertinib mesylate

TABLE 23

| Compression force (kN) | Pre-compression force (kN) | Hardness (N) | Thickness (mm) | Weight (mg) | Friability (%) | Disintegration time (min)* |
|---|---|---|---|---|---|---|
| 7.34 | 1.0 | 174-191 | 7.65-7.79 | 1135-1150 | 0.17 | 0.17 |
| 9.97 | 1.0 | 227-259 | 7.29-7.36 | 1134-1155 | 0.04 | 0.25 |
| 12.54 | 1.0 | 285-312 | 7.04-7.08 | 1138-1153 | NT | 0.22 |
| 17.05 | 1.0 | 356-390 | 7.29-7.36 | 1134-1155 | NT | 0.33 |

*n = 6;
NT = Not tested

Figure 8:
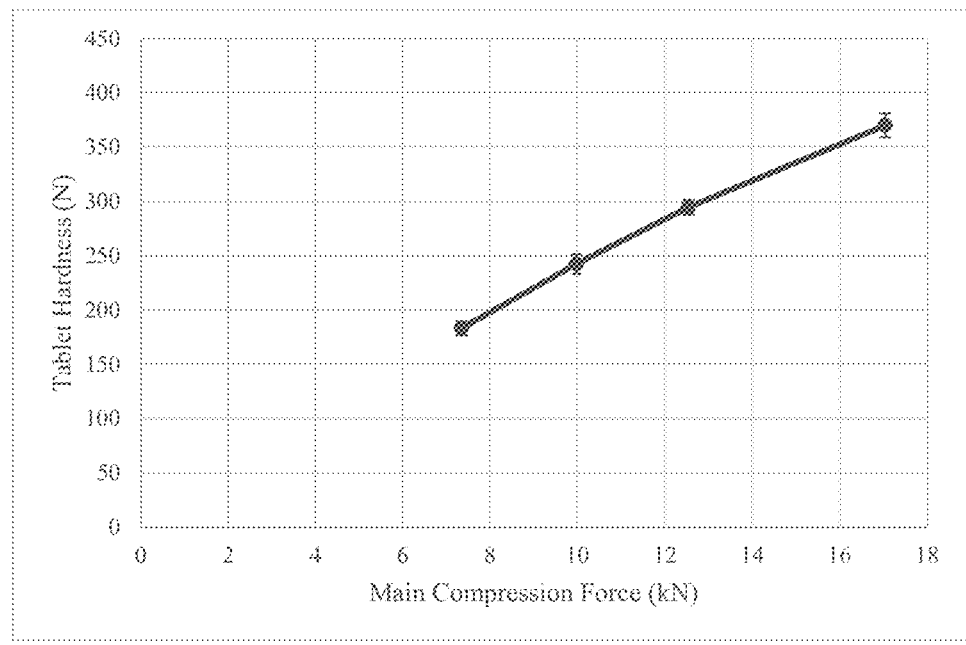
FIG. 8 illustrates the results of a compression force profile study of a further composition according to the present disclosure.

FIG. 8 illustrates the results of a compression force profile study of the composition according to Table 22.

Example 10

Using the manufacturing and compression testing procedures described for the inventive compositions in Example 1, a further inventive composition representing a 240 mg lazertinib tablet was prepared and tested. Table 24 lists the components and their amounts within the tablet, and Table 25 provides the results of compression testing of the composition.

TABLE 24

| Components | Mg/tablet | % w/w |
|---|---|---|
| Lazertinib mesylate[1] | 281.58[1] | 19.97 |
| Microcrystalline cellulose (Vivapur 112) | 201.87 | 14.32 |
| Microcrystalline cellulose (Avicel PH 102) | 671.4 | 47.62 |
| Mannitol (pearlitol SD 200) | 198.0 | 14.04 |
| Croscarmellose sodium (Ac-di-sol) | 36.0 | 2.55 |
| Silica hydrophobic colloidal (Aerosil R972) | 7.05 | 0.5 |
| Magnesium stearate | 14.1 | 1.0 |
| Av. Weight of core tablet | 1410.0 | 100 |

[1]240 mg of lazertinib per tablet is equivalent to 281.58 mg of lazertinib mesylate

TABLE 25

| Compression force (kN) | Pre-compression force (kN) | Hardness (N) | Thickness (mm) | Weight (mg) | Friability (%) | Disintegration time (min)* |
|---|---|---|---|---|---|---|
| 10 | 1.0 | 184-208 | 8.98-9.01 | 1413-1418 | NT | 0.35 |
| 15 | 1.0 | 330-341 | 8.36-8.39 | 1411-1417 | NT | 0.35 |
| 20 | 1.0 | 478-796 | 7.85-7.86 | 1411-1416 | NT | 0.63 |

NT = not tested

Figure 9:
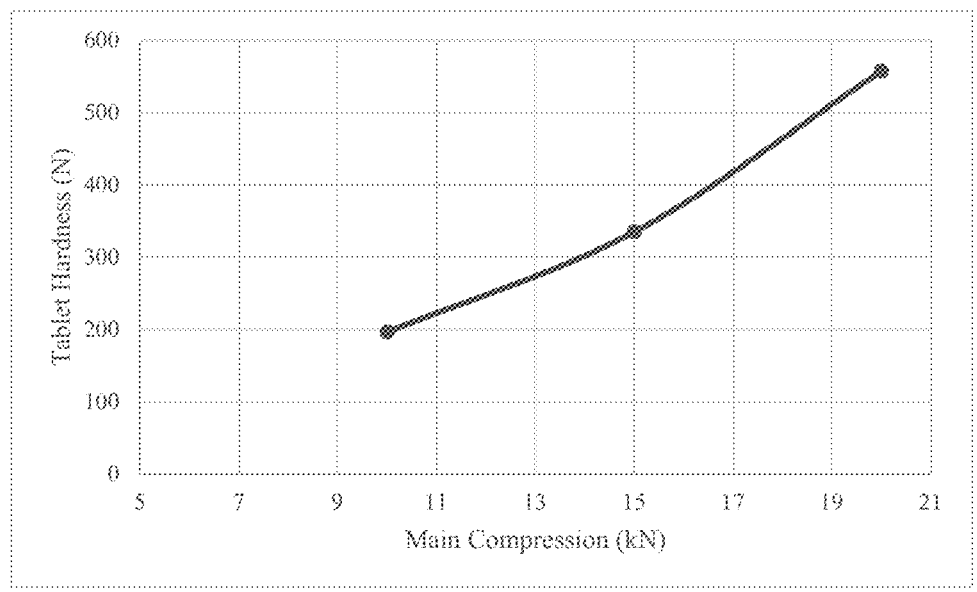
FIG. 9 illustrates the results of a compression force profile study of a further composition according to the present disclosure.

FIG. 9 illustrates the results of a compression force profile study of the composition according to Table 24.

Example 11

Using the manufacturing and compression testing procedures described for the inventive compositions in Example 1, a further inventive composition representing a 120 mg lazertinib tablet was prepared and tested. Table 26 lists the components and their amounts within the tablet, and Table 27 provides the proposed results of compression testing of the composition, i.e., compression is expressed as target conditions only—no compression profile was generated at this scale.

TABLE 26

| Components | Mg/tablet | % w/w |
|---|---|---|
| Lazertinib mesylate [1] | 140.79 [1] | 19.97 |
| Microcrystalline cellulose (Vivapur 112) | 100.94 | 14.32 |
| Microcrystalline cellulose (Avicel PH 102) | 335.7 | 47.62 |
| Mannitol (pearlitol SD 200) | 99 | 14.04 |
| Croscarmellose sodium (Ac-di-sol) | 18 | 2.55 |
| Silica hydrophobic colloidal (Aerosil R972) | 3.5 | 0.5 |
| Magnesium stearate | 7.05 | 1.0 |
| Av. Weight of core tablet | 705.0 | 100 |

[1] 120 mg of lazertinib per tablet is equivalent to 140.79 mg of lazertinib mesylate

TABLE 27

| Compression force (kN) | Pre-compression force (kN) | Hardness (N) | Thickness (mm) | Weight (mg) | Friability (%) | Disintegration time (min)* |
|---|---|---|---|---|---|---|
| 7.5 | 1.0 | 192-208 | 6.25-6.38 | 697.99-709.35 | NT | NT |

*NT = Not tested

Example 12

Using the manufacturing and compression testing procedures described above in Example 1, additional compositions according to the present disclosure are prepared using the ingredients and respective proportions as described in Tables 28-31, below.

TABLE 28

| Components | Mg/tablet | % w/w |
|---|---|---|
| Lazertinib mesylate [1] | 187.72 [1] | 19.97 |
| Microcrystalline cellulose (Vivapur 112) | 134.58 | 14.32 |
| Microcrystalline cellulose (Avicel PH 102) | 447.6 | 47.62 |
| Mannitol (pearlitol SD 200) | 132.0 | 14.04 |
| Croscarmellose sodium (Ac-di-sol) | 24.0 | 2.55 |
| Silica hydrophobic colloidal (Aerosil R972) | 4.7 | 0.5 |
| Magnesium stearate | 9.4 | 1.0 |
| Av. Weight of core tablet | 940.0 | 100 |

[1] 160 mg of lazertinib per tablet is equivalent to 187.72 mg of lazertinib mesylate

TABLE 29

| Components | Mg/tablet | % w/w |
|---|---|---|
| Lazertinib mesylate [1] | 187.72 [1] | 19.97 |
| Microcrystalline cellulose (Vivapur 112) | 139.28 | 14.32 |
| Microcrystalline cellulose (Avicel PH 102) | 447.6 | 48.12 |
| Mannitol (pearlitol SD 200) | 132.0 | 14.04 |
| Croscarmellose sodium (Ac-di-sol) | 24.0 | 2.55 |
| Silica hydrophobic colloidal (Aerosil R972) | — | — |
| Magnesium stearate | 9.4 | 1.0 |
| Av. Weight of core tablet | 940.0 | 100 |

[1] 160 mg of lazertinib per tablet is equivalent to 187.72 mg of lazertinib mesylate

TABLE 30

| Components | Mg/tablet | % w/w |
|---|---|---|
| Lazertinib mesylate [1] | 187.72 [1] | 19.97 |
| Microcrystalline cellulose (Vivapur 112) | — | — |
| Microcrystalline cellulose (Avicel PH 102) | 582.18 | 61.93 |
| Mannitol (pearlitol SD 200) | 132.0 | 14.04 |
| Croscarmellose sodium (Ac-di-sol) | 24.0 | 2.55 |
| Silica hydrophobic colloidal (Aerosil R972) | 4.7 | 0.5 |
| Magnesium stearate | 9.4 | 1.0 |
| Av. Weight of core tablet | 940.0 | 100 |

[1] 160 mg of lazertinib per tablet is equivalent to 187.72 mg of lazertinib mesylate

TABLE 31

| Components | Mg/tablet | % w/w |
|---|---|---|
| Lazertinib mesylate [1] | 187.72 [1] | 24.70 |
| Microcrystalline cellulose (Vivapur 112) | — | — |
| Microcrystalline cellulose (Avicel PH 102) | 441.88 | 58.14 |
| Mannitol (pearlitol SD 200) | 100 | 13.16 |
| Croscarmellose sodium (Ac-di-sol) | 19 | 2.5 |
| Silica hydrophobic colloidal (Aerosil R972) | 3.8 | 0.5 |
| Magnesium stearate | 7.6 | 1.0 |
| Av. Weight of core tablet | 760.00 | 100 |

[1] 160 mg of lazertinib per tablet is equivalent to 187.72 mg of lazertinib mesylate

Example 13

Using the manufacturing and compression testing procedures described above in Example 1, additional compositions according to the present disclosure are prepared using the ingredients and respective proportions as described in Tables 32-34, below.

TABLE 32

| Components | Mg/tablet | % w/w |
|---|---|---|
| Lazertinib mesylate [1] | 281.58 [1] | 19.97 |
| Microcrystalline cellulose (Vivapur 112) | 201.87 | 14.32 |
| Microcrystalline cellulose (Avicel PH 102) | 678.45 | 48.12 |
| Mannitol (pearlitol SD 200) | 198.0 | 14.04 |
| Croscarmellose sodium (Ac-di-sol) | 36.0 | 2.55 |
| Silica hydrophobic colloidal (Aerosil R972) | — | — |
| Magnesium stearate | 14.1 | 1.0 |
| Av. Weight of core tablet | 1410.0 | 100 |

[1] 240 mg of lazertinib per tablet is equivalent to 281.58 mg of lazertinib mesylate

TABLE 33

| Components | Mg/tablet | % w/w |
|---|---|---|
| Lazertinib mesylate [1] | 281.58 [1] | 19.97 |
| Microcrystalline cellulose (Vivapur 112) | — | — |
| Microcrystalline cellulose (Avicel PH 102) | 873.27 | 61.93 |
| Mannitol (pearlitol SD 200) | 198.0 | 14.04 |
| Croscarmellose sodium (Ac-di-sol) | 36.0 | 2.55 |
| Silica hydrophobic colloidal (Aerosil R972) | 7.05 | 0.5 |
| Magnesium stearate | 14.1 | 1.0 |
| Av. Weight of core tablet | 1410.0 | 100 |

[1] 240 mg of lazertinib per tablet is equivalent to 281.58 mg of lazertinib mesylate

TABLE 34

| Components | Mg/tablet | % w/w |
|---|---|---|
| Lazertinib mesylate [1] | 281.58 [1] | 24.70 |
| Microcrystalline cellulose (Vivapur 112) | — | — |
| Microcrystalline cellulose (Avicel PH 102) | 662.82 | 58.14 |
| Mannitol (pearlitol SD 200) | 150.0 | 13.16 |
| Croscarmellose sodium (Ac-di-sol) | 28.5 | 2.5 |
| Silica hydrophobic colloidal (Aerosil R972) | 5.7 | 0.5 |
| Magnesium stearate | 11.4 | 1.0 |
| Av. Weight of core tablet | 1140.00 | 100 |

[1] 240 mg of lazertinib per tablet is equivalent to 281.58 mg of lazertinib mesylate

Example 14

Using the manufacturing and compression testing procedures described above in Example 1, additional compositions according to the present disclosure are prepared using the ingredients and respective proportions as described in Tables 35-38, below.

TABLE 35

| Components | Mg/tablet | % w/w |
|---|---|---|
| Lazertinib mesylate [1] | 140.79 [1] | 19.97 |
| Microcrystalline cellulose (Vivapur 112) | 100.94 | 14.32 |
| Microcrystalline cellulose (Avicel PH 102) | 339.23 | 48.12 |
| Mannitol (pearlitol SD 200) | 99 | 14.04 |
| Croscarmellose sodium (Ac-di-sol) | 18 | 2.55 |
| Silica hydrophobic colloidal (Aerosil R972) | — | — |
| Magnesium stearate | 7.05 | 1.0 |
| Av. Weight of core tablet | 705.0 | 100 |

[1] 120 mg of lazertinib per tablet is equivalent to 140.79 mg of lazertinib mesylate

TABLE 36

| Components | Mg/tablet | % w/w |
|---|---|---|
| Lazertinib mesylate [1] | 140.79 [1] | 19.97 |
| Microcrystalline cellulose (Vivapur 112) | — | — |
| Microcrystalline cellulose (Avicel PH 102) | 436.64 | 61.93 |
| Mannitol (pearlitol SD 200) | 99 | 14.04 |
| Croscarmellose sodium (Ac-di-sol) | 18 | 2.55 |
| Silica hydrophobic colloidal (Aerosil R972) | 3.5 | 0.5 |
| Magnesium stearate | 7.05 | 1.0 |
| Av. Weight of core tablet | 705.0 | 100 |

[1] 120 mg of lazertinib per tablet is equivalent to 140.79 mg of lazertinib mesylate

TABLE 37

| Components | Mg/tablet | % w/w |
|---|---|---|
| Lazertinib mesylate [1] | 140.79 [1] | 24.70 |
| Microcrystalline cellulose (Vivapur 112) | — | — |
| Microcrystalline cellulose (Avicel PH 102) | 331.41 | 58.14 |
| Mannitol (pearlitol SD 200) | 75.0 | 13.16 |
| Croscarmellose sodium (Ac-di-sol) | 14.25 | 2.5 |
| Silica hydrophobic colloidal (Aerosil R972) | 2.85 | 0.5 |
| Magnesium stearate | 5.7 | 1.0 |
| Av. Weight of core tablet | 570.0 | 100 |

[1] 120 mg of lazertinib per tablet is equivalent to 140.79 mg of lazertinib mesylate

TABLE 38

| Components | Mg/tablet | % w/w |
|---|---|---|
| Lazertinib mesylate [1] | 140.79 [1] | 24.70 |
| Microcrystalline cellulose (Vivapur 112) | — | — |
| Microcrystalline cellulose (Avicel PH 102) | 334.26 | 58.64 |
| Mannitol (pearlitol SD 200) | 75.0 | 13.16 |
| Croscarmellose sodium (Ac-di-sol) | 14.25 | 2.5 |
| Silica hydrophobic colloidal (Aerosil R972) | 2.85 | 0.5 |
| Magnesium stearate | 5.7 | 1.0 |
| Av. Weight of core tablet | 570.0 | 100 |

[1] 120 mg of lazertinib per tablet is equivalent to 140.79 mg of lazertinib mesylate

Example 15

Using the manufacturing and compression testing procedures described above in Example 1, additional compositions according to the present disclosure are prepared using the ingredients and respective proportions as described in Tables 39-41, below. Each of Tables 39-41 provides the pharmaceutical formulation of a film-coated core tablet, in which the coating material is Opadry® QX 321A220024 or Opadry® AMB Yellow 80W62680, as shown, and each core tablet contains Lazertinib mesylate monohydrate, microcrystalline cellulose, mannitol, croscarmellose sodium, colloidal silicon dioxide and magnesium stearate in the amounts shown.

TABLE 39

| Components | Mg/tablet | % w/w of core tablet |
|---|---|---|
| Lazertinib mesylate monohydrate[1] | 96.48[1] | 25.39 |
| Microcrystalline cellulose (Vivapur® 112) | — | — |
| Microcrystalline cellulose (Avicel® PH 102) | 218.32 | 57.45 |
| Mannitol (Pearlitol® SD 200) | 50.00 | 13.16 |
| Croscarmellose sodium | 9.5 | 2.5 |
| Colloidal silicon dioxide (Aerosil® R972) | 1.9 | 0.5 |
| Magnesium stearate | 3.8 | 1.00 |
| Opadry® QX 321A220024 | 11.4 | |
| Average Weight of coated tablet (including core tablet and coating) | 391.4 | |

[1]80 mg of lazertinib per tablet is equivalent to 96.48 mg of lazertinib mesylate monohydrate

TABLE 40

| Components | Mg/tablet | % w/w of core tablet |
|---|---|---|
| Lazertinib mesylate monohydrate[1] | 96.48[1] | 20.53 |
| Microcrystalline cellulose (Vivapur® 112) | 64.67 | 13.76 |
| Microcrystalline cellulose (Avicel® PH 102) | 223.80 | 47.62 |
| Mannitol (Pearlitol® SD 200) | 66.00 | 14.04 |
| Croscarmellose sodium | 12.00 | 2.55 |
| Colloidal silicon dioxide (Aerosil® R972) | 2.35 | 0.5 |
| Magnesium stearate | 4.7 | 1.00 |
| Opadry® AMB Yellow 80W62680 | 14.10 | |
| Average Weight of coated tablet (including core tablet and coating) | 484.10 | |

[1]80 mg of lazertinib per tablet is equivalent to 96.48 mg of lazertinib mesylate monohydrate

TABLE 41

| Components | Mg/tablet | % w/w of core tablet |
|---|---|---|
| Lazertinib mesylate monohydrate[1] | 289.44[1] | 25.39 |
| Microcrystalline cellulose (Vivapur® 112) | — | — |
| Microcrystalline cellulose (Avicel® PH 102) | 654.96 | 57.45 |
| Mannitol (Pearlitol® SD 200) | 150.00 | 13.16 |
| Croscarmellose sodium | 28.50 | 2.5 |
| Colloidal silicon dioxide (Aerosil® R972) | 5.7 | 0.5 |
| Magnesium stearate | 11.4 | 1.00 |
| Opadry® QX 321A220024 | 34.2 | |
| Average Weight of coated tablet (including core tablet and coating) | 1174.2 | |

[1]240 mg of lazertinib per tablet is equivalent to 289.44 mg of lazertinib mesylate monohydrate

What is claimed is:

1. A pharmaceutical composition for oral administration comprising: N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, and/or solvate thereof as an active ingredient; and a combination of (i) a cellulose derivative and (ii) a sugar or polyol as diluents, wherein the cellulose derivative and the sugar or polyol are present in the pharmaceutical composition in a weight ratio of 1:0.20 to 1:0.30, wherein the combination is a dry blend of the cellulose derivative and the sugar or polyol in the absence of a solvent.

2. The pharmaceutical composition of claim 1, wherein the cellulose derivative and the sugar or polyol are present in the pharmaceutical composition in a weight ratio of 1:0.20 to 1:0.25.

3. The pharmaceutical composition of claim 1, wherein the cellulose derivative is microcrystalline cellulose.

4. The pharmaceutical composition of claim 1, wherein the sugar or polyol is mannitol.

5. The pharmaceutical composition of claim 1, further comprising:
croscarmellose sodium as a disintegrating agent.

6. The pharmaceutical composition of claim 5, wherein the croscarmellose sodium is present in a range of 2 to 3 wt %, with respect to the total weight of the composition.

7. The pharmaceutical composition of claim 1, further comprising: magnesium stearate as a lubricant.

8. The pharmaceutical composition of claim 1, further comprising croscarmellose sodium as a disintegrating agent, and magnesium stearate as a lubricant.

9. The pharmaceutical composition of claim 1, wherein the active ingredient is N-(5-(4-(4-((dimethylamino)methyl)-3-phenyl-1H-pyrazol-1-yl)pirimidine-2-ylamino)-4-methoxy-2-morpholinophenyl)acrylamide mesylate monohydrate.

10. The pharmaceutical composition of claim 9, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate monohydrate is a crystalline form having a PXRD pattern with peaks at 5.614, 12.394, 14.086, 17.143, 18.020, 19.104, 21.585, 22.131, and 22.487°2θ±0.2°2θ.

11. The pharmaceutical composition of claim 9, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate monohydrate is a crystalline form having a differential scanning calorimeter (DSC) thermogram with an endothermic peak at 210 to 230° C.

12. The pharmaceutical composition of claim 1, wherein the pharmaceutical composition comprises 15-40 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 55-80 wt % of the combination of microcrystalline cellulose and mannitol; 2-3 wt % of croscarmellose sodium; and 0.5 to 2 wt % of magnesium stearate.

13. The pharmaceutical composition of claim 1, wherein the pharmaceutical composition comprises 17-38 wt % of N-(5-(4-(4-((dimethylamino)methyl)-3-phenyl-1H-pyrazol-1-yl)pirimidine-2-ylamino)-4-methoxy-2-morpholinophenyl)acrylamide mesylate; 60 to 77 wt % of the combination of microcrystalline cellulose and mannitol; 2.5-3 wt % of croscarmellose sodium; and 0.75-1.25 wt % of magnesium stearate.

14. The pharmaceutical formulation according to claim 1, further comprising colloidal silicon dioxide.

15. The pharmaceutical formulation according to claim 14, wherein the colloidal silicon dioxide is hydrophobic colloidal silicone dioxide.

16. The pharmaceutical formulation according to claim 14, wherein the colloidal silicone dioxide is present in an amount of about 0.50 wt %, based on the total weight of the pharmaceutical formulation.

17. The pharmaceutical composition of claim 13, wherein N-(5-(4-(4-((dimethylamino)methyl)-3-phenyl-1H-pyrazol-1-yl)pirimidine-2-ylamino)-4-methoxy-2-morpholinophenyl)acrylamide mesylate is a crystalline form having a differential scanning calorimeter (DSC) thermogram with an endothermic peak at 217±2° C.

18. The pharmaceutical formulation according to claim 1, wherein the active ingredient is present in the pharmaceutical formulation in a weight ratio of 1:1.5 to 1:4 relative to the combination of diluents.

19. The pharmaceutical formulation according to claim 1, wherein the active ingredient is present in the pharmaceutical formulation in a weight ratio of 1:1.8 to 1:3.9 relative to the combination of diluents.

20. The pharmaceutical formulation according to claim 1, wherein the active ingredient is present in an amount of 15-35 wt %, relative to the total weight of the pharmaceutical formulation.

21. The pharmaceutical formulation according to claim 1, wherein the active ingredient is present in an amount of 18-35 wt %, relative to the total weight of the pharmaceutical formulation.

22. The pharmaceutical formulation according to claim 1, wherein the active ingredient is present in an amount of about 20 wt %, relative to the total weight of the pharmaceutical formulation.

23. The pharmaceutical formulation according to claim 1, wherein the active ingredient is present in an amount of about 25 wt %, relative to the total weight of the pharmaceutical formulation.

24. The pharmaceutical composition of claim 15, wherein the Lazertinib or a pharmaceutically acceptable salt, hydrate, or solvate thereof and the hydrophobic colloidal silicone dioxide are combined prior to addition of the combination of a cellulose derivative and a sugar or polyol.

25. A pharmaceutical composition for oral administration comprising:
   (a) N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, and/or solvate thereof as an active ingredient;
   (b) hydrophobic colloidal silica;
   (c) croscarmellose sodium as a disintegrating agent;
   (d) magnesium stearate; and
   (e) a combination of (i) a cellulose derivative and (ii) a sugar or polyol as diluents, wherein the cellulose derivative and the sugar or polyol are present in the pharmaceutical composition in a weight ratio of 1:0.10 to 1:0.40.

26. The pharmaceutical composition of claim 25, wherein the pharmaceutical composition comprises:
   (a) N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, and/or solvate thereof in amount equivalent to about 80 mg Lazertinib free base;
   (b) hydrophobic colloidal silicone dioxide in an amount of about 0.25-0.75 wt %;
   (c) croscarmellose sodium in an amount of about 1-5 wt. %;
   (d) magnesium stearate in an amount of about 0.75-1.25 wt %; and
   (e) cellulose derivative and sugar or polyol in an amount of about 62-80 wt %.

27. The pharmaceutical composition of claim 25, wherein the pharmaceutical composition comprises:
   (a) N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, and/or solvate thereof in amount equivalent to about 240 mg Lazertinib free base;
   (b) hydrophobic colloidal silicone dioxide in an amount of about 0.25-0.75 wt %;
   (c) croscarmellose sodium in an amount of about 1-5 wt. %;
   (d) magnesium stearate in an amount of about 0.75-1.25 wt %; and
   (e) cellulose derivative and sugar or polyol in an amount of about 62-80 wt %.

28. A method for manufacturing a pharmaceutical composition comprising:
   (a) blending N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or a pharmaceutically acceptable salt, hydrate, and/or solvate thereof with hydrophobic colloidal silicone dioxide;
   (b) adding mannitol, microcrystalline cellulose and croscarmellose sodium to the mixture of (a) and blending;
   (c) adding magnesium stearate to the mixture of (b) and blending; and
   (d) compressing the mixture of step (c) into a tablet.

* * * * *